(12) United States Patent
Harikrishnan et al.

(10) Patent No.: US 12,012,374 B2
(45) Date of Patent: Jun. 18, 2024

(54) AGONISTS OF ROR GAMMAt

(71) Applicant: BRISTOL-MYERS SQUIBB COMPANY, Princeton, NJ (US)

(72) Inventors: Lalgudi S. Harikrishnan, Skillman, NJ (US); Muthoni G. Kamau, Lawrenceville, NJ (US); Brian E. Fink, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 396 days.

(21) Appl. No.: 17/610,548

(22) PCT Filed: May 7, 2020

(86) PCT No.: PCT/US2020/031747
§ 371 (c)(1),
(2) Date: Nov. 11, 2021

(87) PCT Pub. No.: WO2020/231713
PCT Pub. Date: Nov. 19, 2020

(65) Prior Publication Data
US 2023/0242478 A1    Aug. 3, 2023

Related U.S. Application Data

(60) Provisional application No. 62/846,780, filed on May 13, 2019.

(51) Int. Cl.
| C07D 207/12 | (2006.01) |
| C07C 317/22 | (2006.01) |
| C07D 401/06 | (2006.01) |
| C07D 403/06 | (2006.01) |
| C07D 407/06 | (2006.01) |
| C07D 409/06 | (2006.01) |
| C07D 417/06 | (2006.01) |

(52) U.S. Cl.
CPC .......... *C07C 317/22* (2013.01); *C07D 207/12* (2013.01); *C07D 401/06* (2013.01); *C07D 403/06* (2013.01); *C07D 407/06* (2013.01); *C07D 409/06* (2013.01); *C07D 417/06* (2013.01)

(58) Field of Classification Search
None
See application file for complete search history.

(56) References Cited

FOREIGN PATENT DOCUMENTS

| WO | 2015103508 A1 | 7/2015 |
| WO | 2015103509 A1 | 7/2015 |

OTHER PUBLICATIONS

Lalgudi, et al., "Substituted benzyloxytricyclic compounds as retinoic acid-related orphan receptor gamma t (RORyt) agonists", Bioorganic and Medicinal Chemistry Letters, 2020, vol. 30, pp. 127204.

*Primary Examiner* — Samantha L Shterengarts
(74) *Attorney, Agent, or Firm* — Elliott Korsen

(57) ABSTRACT

The present invention is directed to compounds of the formula wherein all substituents are defined herein, as well as pharmaceutically acceptable compositions comprising compounds of the invention and methods of using said compositions in the treatment of various disorders.

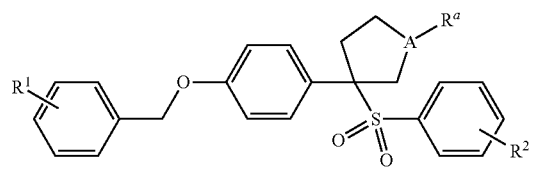

10 Claims, No Drawings

AGONISTS OF ROR GAMMAt

CROSS-REFERENCE TO RELATED APPLICATIONS

This application claims the benefit of U.S. Provisional Application No. 62/846,780, filed May 13, 2019, the disclosure of which is incorporated herein by reference in its entirety.

FIELD OF THE INVENTION

The invention provides novel compounds, pharmaceutical compositions comprising the compounds, and methods of using them, for example, for the treatment or prophylaxis of certain cancers and to their use in therapy.

BACKGROUND OF THE INVENTION

RORgamma t (RORgt, RORγt) is a key lineage-defining transcription factor involved in the differentiation of naïve T cells to Th17 and Tc17 cells. IL-17 is a signature cytokine of RORgt transactivation (Ivanov et al; Cell 2006, 126, 1121).

High IL-17 levels have been associated with various autoimmune diseases. Consequently, several groups have identified RORgt inverse agonists to decrease IL-17 production aimed at suppressing immunity to treat various autoimmune diseases, most notably psoriasis (Bronner et al. *Expert Opin. Ther. Pat.* 2017, 27, 1, 101)

More recently RORgt agonism has been reported to increase the production of antitumor cytokines and chemokines (such as IL-17A and GM-CSF), as well as augment the expression of co-stimulatory receptors (such as CD137 and CD226) and decrease the levels of co-inhibitory receptors (such as PD1 and TIGIT) (Hu et al. *Oncoimmunology*, 2016, 5, 12, e1254854). High levels of Th17 cells or IL-17 has been associated with patient survival in certain cancers (Kryczek et al. *Blood* 2009, 114, 1141; Sfanos et al. *Clin. Can. Res.* 2008, 14, 3254). Therefore RORgt agonism has the potential to boost immune response to tumors and thus confer durable antitumor response. A recent review (Qiu et al *J. Med. Chem.* 2018, 61, 5794) summarizes the progress by various research groups towards the identification of RORgt agonists.

The present invention, therefore, provides novel aryl sulfone compounds which may be useful for the treatment of cancer.

SUMMARY OF THE INVENTION

There is provided a compound of formula (I)

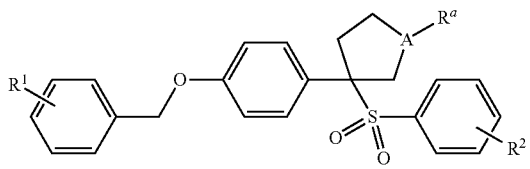

(I)

wherein all substituents are defined herein.

In another aspect, there is provided a pharmaceutical composition comprising a compound of the invention or a pharmaceutically acceptable salt thereof and one or more pharmaceutically acceptable carriers, diluents or excipients.

In another aspect, there is provided a method of treating cancer which comprises administering to a subject in need thereof a therapeutically effective amount of an agonist of RORγ.

DETAILED DESCRIPTION OF THE INVENTION

The following are aspects and embodiments of the present invention, as well as additional aspects and embodiments that can be within the scope of those shown. The aspects of the invention are not limited to those described below.

In a first aspect, there is disclosed a compound of formula I

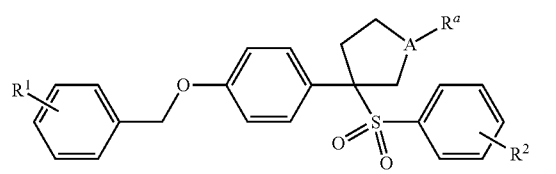

(I)

wherein
- A is —CH— or —N—;
- $R^a$ is H or CO—$R^b$,
- $R^b$ is a $C_{3-8}$ cycloalkyl or a —$(CH_2)_r$-3-7 membered heterocycle either of which is substituted with 0-3 $R^c$;
- $R^c$ is halogen, $C_{1-6}$ alkyl, COOH or $CONH_2$,
- $R^1$ and $R^2$ are independently 0-4 hydrogen, halogen, $C_{1-6}$ alkyl or $CF_3$;
- r is 0, 1 or 2;
- or a pharmaceutically acceptable salt thereof.

In a second aspect, there is disclosed a compound of the formula

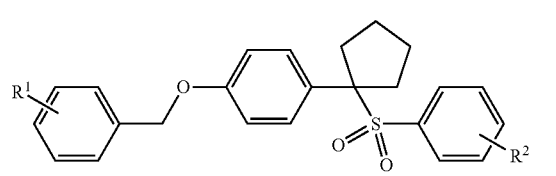

(II)

wherein
- $R^1$ and $R^2$ are independently 0-4 hydrogen, halogen, $C_{1-6}$ alkyl or $CF_3$; or a pharmaceutically acceptable salt thereof.

In a third aspect, there is disclosed a compound of the formula

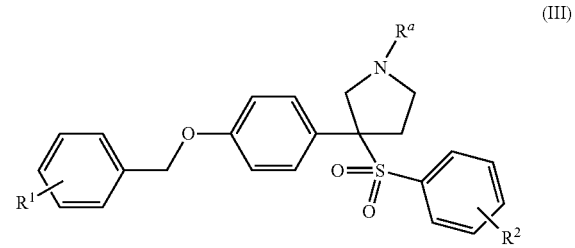

(III)

wherein
R$^a$ is CO—R$^b$,
R$^b$ is a C$_{3-8}$ cycloalkyl or a —(CH$_2$)$_r$-3-7 membered heterocycle either of which is substituted with 0-3 R$^c$;
R$^c$ is hydrogen, halogen, C$_{1-6}$ alkyl, COOH or CONH$_2$,
R$^1$ and R$^2$ are independently 0-4 hydrogen, halogen, C$_{1-6}$ alkyl or CF$_3$;
r is 0, 1 or 2;
or a pharmaceutically acceptable salt thereof.

In a fourth aspect, there is disclosed a compound of formula (III) wherein
R$^a$ is CO—R$^b$,
R$^b$ is a C$_{3-8}$ cycloalkyl substituted with 0-3 R$^c$;
R$^c$ is hydrogen, halogen, C$_{1-6}$ alkyl, COOH or CONH$_2$,
R$^1$ and R$^2$ are independently 0-4 hydrogen, halogen, C$_{1-6}$ alkyl or CF$_3$;
or a pharmaceutically acceptable salt thereof.

In a fifth aspect, there is disclosed a compound of formula (III) wherein
R$^a$ is CO—R$^b$,
R$^b$ is a —(CH$_2$)$_r$-3-7 membered heterocycle substituted with 0-3 R$^c$;
R$^c$ is hydrogen, halogen, C$_{1-6}$ alkyl, COOH or CONH$_2$,
R$^1$ and R$^2$ are independently 0-4 hydrogen, halogen, C$_{1-6}$ alkyl or CF$_3$;
r is 0, 1 or 2;
or a pharmaceutically acceptable salt thereof.

In a sixth aspect, there is disclosed a compound of formula (III) wherein
R$^a$ is CO—R$^b$,
R$^b$ is a —(CH$_2$)$_r$-3-7 membered heterocycle substituted with 0-3 R$^c$;
R$^c$ is hydrogen, halogen, C$_{1-6}$ alkyl, COOH or CONH$_2$,
R$^1$ and R$^2$ are independently 0-4 hydrogen, halogen, C$_{1-6}$ alkyl or CF$_3$;
r is 1;
or a pharmaceutically acceptable salt thereof.

In a seventh aspect, there is disclosed a compound of formula (III) wherein
R$^a$ is CO—R$^b$,
R$^b$ is a —(CH$_2$)$_r$-3-7 membered heterocycle substituted with 0-3 R$^c$, wherein the heterocycle is selected from the group consisting of oxanyl, pyridinyl, triazolyl, thiolane-1,1-dione, thiazolidine-2,4-dione or thiane-1,1-dione;
R$^c$ is hydrogen, halogen, C$_{1-6}$ alkyl, COOH or CONH$_2$,
R$^1$ and R$^2$ are independently 0-4 hydrogen, halogen, C$_{1-6}$ alkyl or CF$_3$;
r is 1;
or a pharmaceutically acceptable salt thereof.

In another aspect, there is provided the following compounds of the invention
1-(benzyloxy)-4-(1-(((4-fluorophenyl)sulfonyl)cyclopentyl)benzene,
4-{3-[4-(benzyloxy)phenyl]-3-(4-fluorobenzenesulfonyl)pyrrolidine-1-carbonyl}-1lambda6-thiane-1,1-dione, (2)
4-[(3R)-3-(4-{[2-fluoro-6-(trifluoromethyl)phenyl]methoxy}phenyl)-3-(4-fluorobenzenesulfonyl)pyrrolidine-1-carbonyl]-1lambda6-thiane-1,1-dione, (3)
1-[1-(4-fluorobenzenesulfonyl)cyclopentyl]-4-(2-phenylethoxy)benzene, (4)
1-(benzyloxy)-4-[1-(3-chlorobenzenesulfonyl)cyclopentyl]benzene,
1-[1-(benzenesulfonyl)cyclopentyl]-4-(benzyloxy)benzene,
1-[1-(4-fluorobenzenesulfonyl)cyclopentyl]-4-[(2-fluorophenyl)methoxy]benzene,
1-(benzyloxy)-4-{1-[3-(trifluoromethyl)benzenesulfonyl]cyclopentyl}benzene,
1-(benzyloxy)-4-[1-(4-chlorobenzenesulfonyl)cyclopentyl]benzene,
1-[1-(benzenesulfonyl)cyclopentyl]-4-(cyclohexylmethoxy)benzene, (10)
1-[1-(benzenesulfonyl)cyclopentyl]-4-[(3-fluorophenyl)methoxy]benzene,
1-[1-(benzenesulfonyl)cyclopentyl]-4-[(4-fluorophenyl)methoxy]benzene,
1-[1-(benzenesulfonyl)cyclopentyl]-4-[(2-fluorophenyl)methoxy]benzene,
1-[1-(benzenesulfonyl)cyclopentyl]-4-(2-cyclopropylethoxy)benzene, (14)
1-{3-[4-(benzyloxy)phenyl]-3-(4-fluorobenzenesulfonyl)pyrrolidin-1-yl}-2-(oxan-4-yl)ethan-1-one,
1-{3-[4-(benzyloxy)phenyl]-3-(4-fluorobenzenesulfonyl)pyrrolidin-1-yl}-2-(pyridin-4-yl)ethan-1-one,
1-{3-[4-(benzyloxy)phenyl]-3-(4-fluorobenzenesulfonyl)pyrrolidin-1-yl}-2-(1H-1,2,3-triazol-1-yl)ethan-1-one,
3-[4-(benzyloxy)phenyl]-3-(4-fluorobenzenesulfonyl)-1-(oxane-4-carbonyl)pyrrolidine,
3-{3-[4-(benzyloxy)phenyl]-3-(4-fluorobenzenesulfonyl)pyrrolidine-1-carbonyl}-1λ$^6$-thiolane-1,1-dione,
5-(2-{3-[4-(benzyloxy)phenyl]-3-(4-fluorobenzenesulfonyl)pyrrolidin-1-yl}-2-oxoethyl)-1,3-thiazolidine-2,4-dione,
4-{3-[4-(benzyloxy)phenyl]-3-[3-(trifluoromethyl)benzenesulfonyl]pyrrolidine-1-carbonyl}-1λ$^6$-thiane-1,1-dione,
1-{3-[4-(benzyloxy)phenyl]-3-[3-(trifluoromethyl)benzenesulfonyl]pyrrolidin-1-yl}-2-(pyridin-4-yl)ethan-1-one,
4-[3-(benzenesulfonyl)-3-{4-[(2,6-dichlorophenyl)methoxy]phenyl}pyrrolidine-1-carbonyl]-1λ$^6$-thiane-1,1-dione,
(1r,4r)-4-[3-(benzenesulfonyl)-3-{4-[(2,6-dichlorophenyl)methoxy]phenyl}pyrrolidine-1-carbonyl]cyclohexane-1-carboxylic acid,
4-[3-(benzenesulfonyl)-3-{4-[(2,6-dichlorophenyl)methoxy]phenyl}pyrrolidine-1-carbonyl]piperidine-1-carboxamide,
1-[3-(benzenesulfonyl)-3-{4-[(2,6-dichlorophenyl)methoxy]phenyl}pyrrolidin-1-yl]-2-(pyridin-4-yl)ethan-1-one,
4-[3-(benzenesulfonyl)-3-{4-[(2-chloro-3,6-difluorophenyl)methoxy]phenyl}pyrrolidine-1-carbonyl]-1λ$^6$-thiane-1,1-dione,
4-[3-(benzenesulfonyl)-3-{4-[(2-chlorophenyl)methoxy]phenyl}pyrrolidine-1-carbonyl]-1λ$^6$-thiane-1,1-dione,
4-[3-(benzenesulfonyl)-3-{4-[(2-chloro-6-fluorophenyl)methoxy]phenyl}pyrrolidine-1-carbonyl]-1λ$^6$-thiane-1,1-dione,
4-[3-(benzenesulfonyl)-3-(4-{[2-fluoro-6-(trifluoromethyl)phenyl]methoxy}phenyl)pyrrolidine-1-carbonyl]-1λ$^6$-thiane-1,1-dione,
4-[3-(benzenesulfonyl)-3-{4-[(2-chloro-4-fluorophenyl)methoxy]phenyl}pyrrolidine-1-carbonyl]-1λ$^6$-thiane-1,1-dione,
4-[3-(benzenesulfonyl)-3-(4-{[2-(trifluoromethyl)phenyl]methoxy}phenyl)pyrrolidine-1-carbonyl]-1λ$^6$-thiane-1,1-dione,
4-[(3R)-3-(benzenesulfonyl)-3-{4-[(2,6-dichlorophenyl)methoxy]phenyl}pyrrolidine-1-carbonyl]-1λ$^6$-thiane-1,1-dione,
(1r,4r)-4-[(3R)-3-(benzenesulfonyl)-3-{4-[(2,6-dichlorophenyl)methoxy]phenyl}pyrrolidine-1-carbonyl]cyclohexane-1-carboxylic acid, (1r,4r)-4-[(3R)-3-{4-[(2,6-dichlorophenyl)methoxy]phenyl}-3-(4-fluorobenzenesulfonyl)pyrrolidine-1-carbonyl]cyclohexane-1-carboxylic acid, 4-[(3R)-3-{4-[(2,6-dichlorophenyl)methoxy]phenyl}-3-(4-fluorobenzenesulfonyl)pyrrolidine-1-carbonyl]-1$\lambda^6$-thiane-1,1-dione, 4-[(3R)-3-(4-fluorobenzenesulfonyl)-3-{4-[(1S)-1-phenylethoxy]phenyl}pyrrolidine-1-carbonyl]-1$\lambda^6$-thiane-1,1-dione, (37)

4-[(3R)-3-(4-fluorobenzenesulfonyl)-3-(4-{[2-(trifluoromethyl)phenyl]methoxy}phenyl)pyrrolidine-1-carbonyl]-1$\lambda^6$-thiane-1,1-dione, 4-[(3R)-3-(4-{[2-chloro-6-(trifluoromethyl)phenyl]methoxy}phenyl)-3-(4-fluorobenzenesulfonyl)pyrrolidine-1-carbonyl]-1$\lambda^6$-thiane-1,1-dione, 4-[(3R)-3-(benzenesulfonyl)-3-(4-{[2-fluoro-6-(trifluoromethyl)phenyl]methoxy}phenyl)pyrrolidine-1-carbonyl]-4-hydroxy-1$\lambda^6$-thiane-1,1-dione, (1r,4r)-4-[(3R)-3-(benzenesulfonyl)-3-(4-{[2-fluoro-6-(trifluoromethyl)phenyl]methoxy}phenyl)pyrrolidine-1-carbonyl]cyclohexane-1-carboxylic acid, (1r,4r)-4-[(3R)-3-(4-{[2-fluoro-6-(trifluoromethyl)phenyl]methoxy}phenyl)-3-(4-fluorobenzenesulfonyl)pyrrolidine-1-carbonyl]cyclohexane-1-carboxylic acid, 4-[(3R)-3-(4-{[2-fluoro-6-(trifluoromethyl)phenyl]methoxy}phenyl)-3-(4-fluorobenzenesulfonyl)pyrrolidine-1-carbonyl]-4-hydroxy-1$\lambda^6$-thiane-1,1-dione, (1r,4r)-4-[(3R)-3-(4-{[2-fluoro-6-(trifluoromethyl)phenyl]methoxy}phenyl)-3-(4-fluorobenzenesulfonyl)pyrrolidine-1-carbonyl]cyclohexane-1-carboxamide, (1r,4r)-4-[(3R)-3-(4-{[2-chloro-6-(trifluoromethyl)phenyl]methoxy}phenyl)-3-(4-fluorobenzenesulfonyl)pyrrolidine-1-carbonyl]cyclohexane-1-carboxamide, 4-[(3R)-3-(4-{[2-chloro-6-(trifluoromethyl)phenyl]methoxy}phenyl)-3-(4-fluorobenzenesulfonyl)pyrrolidine-1-carbonyl]-4-hydroxy-1$\lambda^6$-thiane-1,1-dione, (1r,4r)-4-[(3R)-3-(4-{[2-chloro-6-(trifluoromethyl)phenyl]methoxy}phenyl)-3-(4-fluorobenzenesulfonyl)pyrrolidine-1-carbonyl]cyclohexane-1-carboxylic acid or a pharmaceutically acceptable salt thereof.

In another aspect, there is provided the following compounds of the invention

1-[1-(4-fluorobenzenesulfonyl)cyclopentyl]-4-(2-phenylethoxy)benzene, (4)

1-[1-(benzenesulfonyl)cyclopentyl]-4-(cyclohexylmethoxy)benzene, (10)

1-[1-(benzenesulfonyl)cyclopentyl]-4-(2-cyclopropylethoxy)benzene, (14)

4-[(3R)-3-(4-fluorobenzenesulfonyl)-3-{4-[(1S)-1-phenylethoxy]phenyl}pyrrolidine-1-carbonyl]-1$\lambda^6$-thiane-1,1-dione, (37)

or a pharmaceutically acceptable salt thereof.

In another aspect, there is provided a compound selected from any subset list of compounds within the scope of any of the above aspects.

Other Embodiments of the Invention

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including small cell lung cancer, non-small cell lung cancer, colorectal cancer, melanoma, renal cell carcinoma, head and neck cancer, Hodgkin's lymphoma, bladder cancer, esophageal carcinoma, gastric carcinoma, ovarian carcinoma, cervical carcinoma, pancreatic carcinoma, prostate carcinoma, breast cancers, urinary carcinoma, brain tumors such as glioblastoma, non-Hodgkin's lymphoma, acute lymphatic leukemia (ALL), chronic lymphatic leukemia (CLL), acute myeloid leukemia (AML), chronic myeloid leukemia (CML), hepatocellular carcinoma, multiple myeloma, gastrointestinal stromal tumors, mesothelioma, and other solid tumors or other hematological cancers In another embodiment, the invention provides a method for the treatment and/or prophylaxis of various types of cancer, including without limitation, small cell lung cancer, non-small cell lung cancer, colorectal cancer, melanoma, renal cell carcinoma, head and neck cancer, Hodgkin's lymphoma or bladder cancer.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

Therapeutic Applications

The aryl sulfone compounds of the invention induce the expression of pro-inflammatory cytokines such as IL17 in vitro in human cells, animal cells and human blood.

The aryl sulfones of the invention are agonists of RORgt.

The term "agonist" refers to any substance that activates a biologic receptor in vitro or in vivo to provoke a physiological response.

"RORgt" is an abbreviation of "Retinoic acid receptor related Orphan Receptor Gamma t". RORgt is a transcription factor that in humans is encoded by the gene RORC. Since RORgt and RORg have identical ligand binding domains, in the context of small molecule modulators, RORgt and RORg can be used interchangeably. RORgt and RORg are two isoforms produced from the same RORC gene. Activation of RORgt by agonists leads to induction of pro-inflammatory cytokines, including IL-17.

Another object of the present invention is the aryl sulfone of Formula (I), for use in a therapeutic treatment in humans or animals. In particular, the compounds of the present invention may be used for therapeutic or diagnostic applications in human or animal health.

The term "therapeutic agent" refers to one or more substances that are administered to a human or animal in order to achieve some kind of therapeutic effect in that human or animal, including to prevent, cure, or mitigate the effects of, infection or disease, and/or to otherwise improve the health of that human or animal.

The term "monotherapy" refers to the use of a single substance and/or strategy to treat a human or animal in any clinical or medical context, as opposed to the use of multiple substances and/or strategies to treat a human or animal in the same clinical or medical context, regardless of whether the multiple substances and/or strategies are used sequentially in any order or concurrently.

The term "chemotherapeutic agent" herein refers to one or more chemical substances that are administered to a human or animal in order to kill tumors, or slow or stop the growth of tumors, and/or slow or stop the division of cancerous cells and/or prevent or slow metastasis. Chemotherapeutic agents are often administered to treat cancer, but are also indicated for other diseases.

The term "chemotherapy" refers to medical treatment of a human or animal with one or more chemotherapeutic agents (see definition above).

The term "chemoimmunotherapy" refers to the combined use, whether sequentially in any order or concurrently, of chemotherapy substances and/or strategies, and immunotherapy substances and/or strategies. Chemoimmunotherapy is often employed to treat cancer, but can also be employed to treat other diseases.

The term "immune system" refers to the ensemble, or to any one or more components, of the molecules, substances (e.g. bodily fluids), anatomic structures (e.g. cells, tissue and organs) and physiologic processes involved in preventing infection in the body, in protecting the body during infection or during disease, and/or in helping the body to recuperate after infection or disease. A complete definition of "immune system" is beyond the scope of this patent; however, this term should be understood by any ordinary practitioner in the field.

The term "immune agent" refers to any endogenous or exogenous substance that can interact with any one or more components of the immune system. The term "immune agent" includes antibodies, antigens, vaccines and their constituent components, nucleic acids, synthetic drugs, natural or synthetic organic compounds, cytokines, natural or modified cells, synthetic analogs thereof, and/or fragments thereof.

The term "antagonist" refers to any substance that inhibits, counteracts, downregulates, and/or desensitizes a biologic receptor in vitro or in vivo to provoke a physiological response.

The term "immunotherapy" refers to any medical treatment in which one or more components of a human's or animal's immune system is deliberately modulated in order to directly or indirectly achieve some therapeutic benefit, including systemic and/or local effects, and preventative and/or curative effects. Immunotherapy can involve administering one or more immune agents (see definition above), either alone or in any combination, to a human or animal subject by any route (e.g. orally, intravenously, dermally, by injection, by inhalation, etc.), whether systemically, locally or both.

"Immunotherapy" can involve provoking, increasing, decreasing, halting, preventing, blocking or otherwise modulating the production of cytokines, and/or activating or deactivating cytokines or immune cells, and/or modulating the levels of immune cells, and/or delivering one or more therapeutic or diagnostic substances to a particular location in the body or to a particular type of cell or tissue, and/or destroying particular cells or tissue. Immunotherapy can be used to achieve local effects, systemic effects or a combination of both.

The term "immunosuppressed" describes the state of any human or animal subject whose immune system is functionally diminished, deactivated or otherwise compromised, or in whom one or more immune components is functionally diminished, deactivated or otherwise compromised.

"Immunosuppression" can be the cause, consequence or byproduct of disease, infection, exhaustion, malnutrition, medical treatment or some other physiologic or clinical state.

The terms "immunomodulating substance", "immunomodulatory substance", "immunomodulatory agent" and "immunomodulator", used here synonymously, refer to any substance that, upon administration to a human or animal, directly influences the functioning of the immune system of that human or animal. Examples of common immunomodulators include, but are not limited to, antigens, antibodies and small-molecule drugs.

The term "vaccine" refers to a biological preparation administered to a human or animal in order to elicit or enhance a specific immune system response and/or protection against one or more antigens in that human or animal.

The term "vaccination" refers to treatment of a human or animal with a vaccine or to the act of administering a vaccine to a human or animal.

The term "adjuvant" refers to a secondary therapeutic substance that is administered together (either sequentially in any order, or concurrently) with a primary therapeutic substance to achieve some kind of complimentary, synergic or otherwise beneficial effect that could not be achieved through use of the primary therapeutic substance alone. An adjuvant can be used together with a vaccine, chemotherapy, or some other therapeutic substance. Adjuvants can enhance the efficacy of the primary therapeutic substance, reduce the toxicity or side effects of the primary therapeutic substance, or provide some kind of protection to the subject that receives the primary therapeutic substance, such as, but not limited to, improved functioning of the immune system.

In one embodiment, the aryl sulfone of Formula (I) can increase the amount of IL-17 in a subject. This includes but is not limited to IL-17 produced by TH17 cells.

In one embodiment, the aryl sulfone of Formula (I) can be administered as immunotherapy to a human or an animal to induce in vivo production of one or more cytokines that are therapeutically beneficial to that human or animal. This type of immunotherapy could be used alone or in combination with other treatment strategies, whether sequentially in any order, or concurrently. It could be used to prevent, cure, and/or mitigate the effects of infection or disease in that human or animal, and/or to modulate the immune system of that human or animal to achieve some other therapeutic benefit.

In one particular embodiment, the aryl sulfone compounds of the present invention can be used for cytokine induction immunotherapy of immunosuppressed individuals.

In this example, an aryl sulfone of Formula (I) would be administered to an immunosuppressed human or animal subject to induce in vivo production of one or more cytokines that directly or indirectly enhance the immune system of that human or animal. Subjects that might benefit from such treatment include those suffering from autoimmune disorders, immune system deficiencies or defects, microbial or viral infections, infectious diseases, or cancer.

The present invention thus discloses a method for inducing cytokine in immunosuppressed individuals, said method comprising administering to a patient in need thereof an aryl sulfone of Formula (I) or a pharmaceutically acceptable salt or prodrug thereof.

In another embodiment, the aryl sulfone compounds of the present invention can be used for cytokine induction immunotherapy in combination with chemotherapy. In this example, an aryl sulfone of Formula (I) would be administered together with one or more chemotherapeutic agents, sequentially in any order or concomitantly, to a cancer patient to stop the growth of, shrink and/or destroy tumors in that patient. The chemoimmunotherapy resulting from the combination of cytokine induction, provided by the compound(s) of the present invention, and cytotoxicity, provided by the chemotherapeutic agent(s), might be less toxic to the patient, cause fewer side effects in the patient and/or exhibit greater anti-tumor efficacy than would the chemotherapeutic agent(s) when used as monotherapy.

The present invention thus discloses a method for treating cancer, said method comprising administering to a patient in need thereof: a chemotherapeutic agent; and an aryl sulfone of Formula (I) or a pharmaceutically acceptable salt or prodrug thereof.

Another object of the present invention is the aryl sulfone of Formula (I) for use in the treatment of a bacterial infection, a viral infection or a cancer.

As used herein, "cancer" refers to the physiological condition in subjects that is characterized by unregulated or dysregulated cell growth or death. The term "cancer" includes solid tumors and blood-born tumors, whether malignant or benign.

In a preferred embodiment, the cancer is from the following group: small cell lung cancer, non-small cell lung cancer, colorectal cancer, melanoma, renal cell carcinoma, head and neck cancer, Hodgkin's lymphoma or bladder cancer.

The present invention thus discloses a method for treating a bacterial infection, a viral infection or a cancer, said method comprising administering to a patient in need thereof an aryl sulfone of Formula (I) or a pharmaceutically acceptable salt or prodrug thereof.

Another object of the present invention is the aryl sulfone of Formula (I) for use in the treatment of a pathology that may be alleviated by the induction of an immune response via the RORg or RORgt pathway.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colorectal cancers, blood cancers, lung cancers and bone cancers. Examples of such cancer types include neuroblastoma, intestinal carcinoma such as rectal carcinoma, colon carcinomas, familiar adenomatous polyposis carcinoma and hereditary non-polyposis colorectal cancer, esophageal carcinoma, labial carcinoma, larynx carcinoma, nasopharyngeal cancers, oral cavity cancers, salivary gland carcinoma, peritoneal cancers, soft tissue sarcoma, urothelial cancers, sweat gland carcinoma, gastric carcinoma, adenocarcinoma, medullary thyroid carcinoma, papillary thyroid carcinoma, renal carcinoma, kidney parenchymal carcinoma, ovarian carcinoma, cervical carcinoma, uterine corpus carcinoma, endometrial carcinoma, pancreatic carcinoma, prostate carcinoma, testis carcinoma, breast cancers including HER2 Negative, urinary carcinoma, melanoma, brain tumors such as glioblastoma, astrocytoma, meningioma, medulloblastoma and peripheral neuroectodermal tumors, Hodgkin's lymphoma, non-Hodgkin's lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, multiple myeloma, seminoma, osteosarcoma, chondrosarcoma, anal canal cancers, adrenal cortex carcinoma, chordoma, fallopian tube cancer, gastrointestinal stromal tumors, myeloproliferative diseases, mesothelioma, biliary tract cancers, Ewing sarcoma and other rare tumor types.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergistic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s) of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fni4, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM4-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. The PD-1 antibody can be selected from Opdivo (nivolumab), Keytruda (pembrolizumab), PDR001 (Novartis; see WO2015/112900), MEDI-0680 (AMP-514) (AstraZeneca; see WO2012/145493), REGN-2810 (Sanofi/Regeneron; see WO2015/112800), JS001 (Taizhou Junshi), BGB-A317 (Beigene; see WO2015/35606), INCSHR1210 (SHR-1210) (Incyte/Jiangsu Hengrui Medicine; see WO2015/085847), TSR-042 (ANB001) (Tesara/AnaptysBio; see WO2014/179664), GLS-010 (Wuxi/Harbin Gloria Pharmaceuticals), AM-0001 (Armo/Ligand), or STI-1110 (Sorrento; see WO2014/194302). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224 In one aspect, In another aspect, the immuno-oncology agent is a PD-L1 antagonist, such as an antagonistic PD-L1 antibody. The PD-L1 antibody can be selected from Tecentriq (atezolizumab), durvalumab, avelumab, STI-1014 (Sorrento; see WO2013/181634), or CX-072 (CytomX; see WO2016/149201).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intratumoral routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Another object of the present invention is the aryl sulfone of Formula (I) for use in adoptive cellular therapy to treat cancer, immune disorders and infections.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intratumoral, intravenous or epidural injection as, for example, a sterile solution or suspension, or sustained release formulation; (3) topical application, for example, as a cream, ointment, or a controlled release patch or spray applied to the skin; or intratumorally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Formulations of the present invention include those suitable for oral, intratumoral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient.

A compound of the present invention may also be administered as a bolus, electuary or paste.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

In some cases, in order to prolong the effect of a drug, it is desirable to slow the absorption of the drug from subcutaneous, intratumoral or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As used herein, the term "alkyl" or "alkylene" is intended to include both branched and straight-chain saturated aliphatic hydrocarbon groups having the specified number of carbon atoms. For example, "C$_{1-10}$ alkyl" (or alkylene), is intended to include C$_1$, C$_2$, C$_3$, C$_4$, C$_5$, C$_6$, C$_7$, C$_8$, C$_9$, and C$_{10}$ alkyl groups. Additionally, for example, "C$_1$-C$_6$ alkyl" denotes alkyl having 1 to 6 carbon atoms. Alkyl groups can be unsubstituted or substituted so that one or more of its hydrogens are replaced by another chemical group, for example, aryl or heteroaryl groups which are optionally substituted for example with alkyl, halo or haloalkyl. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

The term "cycloalkyl" refers to cyclized alkyl groups, including mono-, bi- or poly-cyclic ring systems. C$_{3-7}$ cycloalkyl is intended to include C$_3$, C$_4$, C$_5$, C$_6$, and C$_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3, 4, 5, 6, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "halo" or "halogen" refers to chloro, bromo, fluoro and iodo.

The terms "heterocycle", "heterocycloalkyl", "heterocyclo", "heterocyclic", or "heterocyclyl" may be used interchangeably and refer to substituted and unsubstituted 3-to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocyclyl" include "heteroaryl" groups, as defined below.

In addition to the heteroaryl groups described below, exemplary monocyclic heterocycle groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

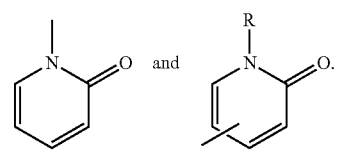

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington: *The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, CA (2008).

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereof as appreciated by those skilled in the art. Preferred methods include, but are not limited to, those described below. All references cited herein are hereby incorporated by reference in their entirety.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Fourth Edition, Wiley and Sons, 2007).

Compounds of Formula (I) may be prepared by reference to the methods illustrated in the following Scheme. As shown therein, the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

Methods of Preparation

Compounds of general formula i can be prepared according to the method outlined in Scheme i. Substituted benzylic halide iA can be reacted with sulfinate iB to provide sulfone iC. Cyclicization of iC using α,ω-dihalide can yield compounds of general formula i.

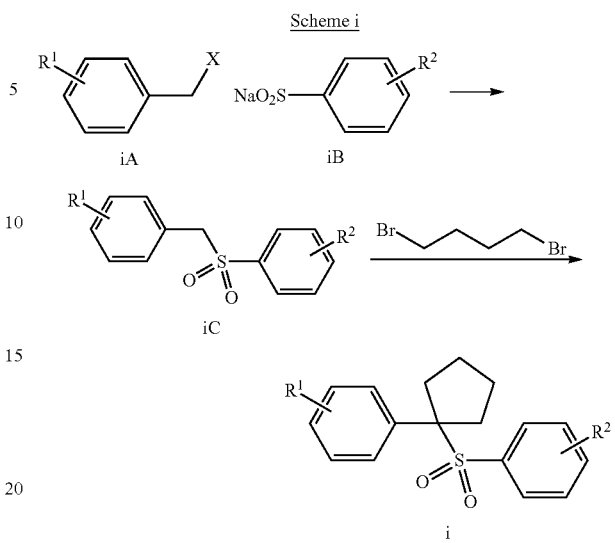

Alternatively, sulfone iC can be condensed with formaldehyde to afford olefin iiA (Scheme ii). Cyclization of olefin iiA can afford protected pyrrolidine iiB. Removal of protecting group in iiB followed by acylation of the resulting amine can yield compounds of general formula ii. The enantiomeric pyrrolidines can be separated at any stage to afford homochiral compounds. It should be noted and obvious to those skilled in the art that intermediates such as iiB, after removal of the protecting group, can be reductively aminated with aldehydes or reacted with various electrophiles such as sulfonyl chlorides, isocyanates or isothiocyanates to yield the corresponding N-substituted compounds.

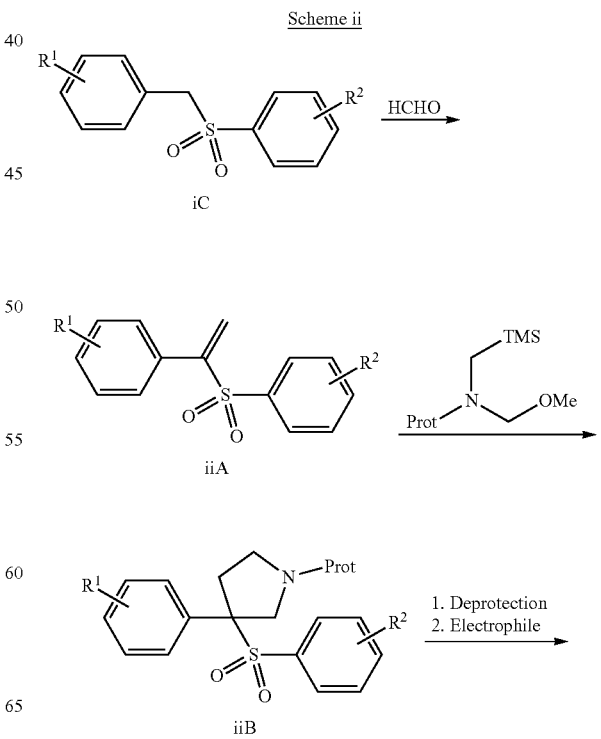

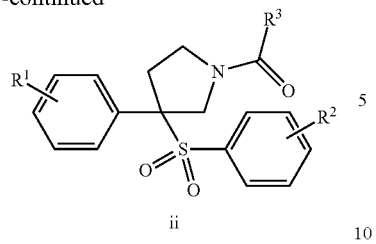

ii

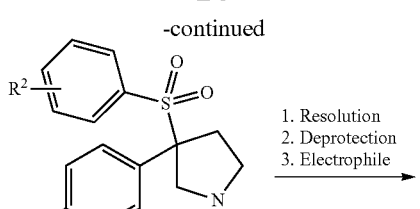

Racemic
iiiE

1. Resolution
2. Deprotection
3. Electrophile

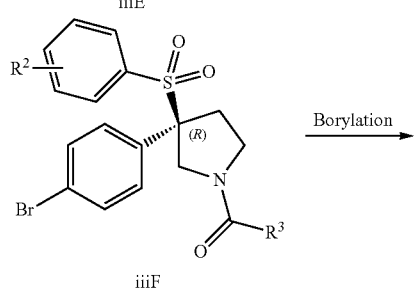

iiiF

Borylation

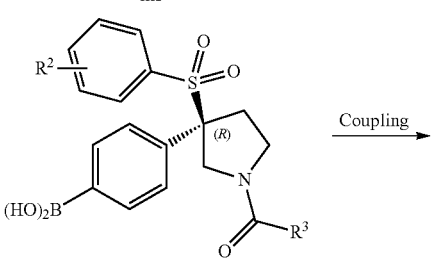

iiiG

Coupling

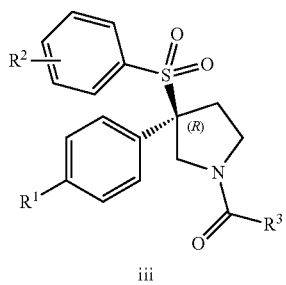

iii

In another variation, sulfone iiiA (that can be accessed via method outlined for iiA) can be condensed with formaldehyde to obtain olefin iiiB (Scheme iii). Michael addition of ethanolamine into olefin iiiB can afford alcohol iiiC. Protection of secondary amine followed by activation of the alcohol can yield protected racemic pyrrolidine iiiE. The enantiomers can be separated at this stage or at any stage after this step to afford homochiral pyrrolidines. Removal of protecting group in iiiE followed by acylation of the resulting amine can yield amide iiiF. Borylation of bromocompound iiiF followed by metal mediated coupling can provide compounds of general formula iii.

Scheme iii

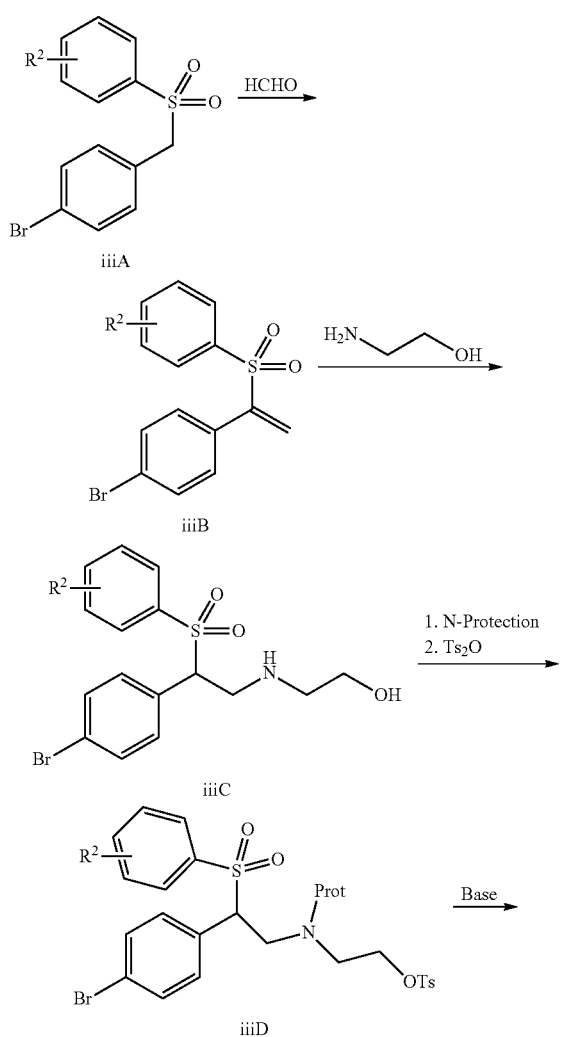

In yet another variation, olefin iiA can be cyclized to afford exomethylene intermediate ivA (Scheme iv). The exp methylele in ivA can undergo a sequence of hydroboration, oxidation and further oxidation to afford racemic carboxylic acid ivB. The enantiomers can be separated at this stage or any stage from this point forward. The carboxylic acid ivB can be coupled with various amines to afford the corresponding amides of general formula iv. The carboxylic acid ivB can undergo Curtius rearrangement to provide the corresponding amine ivC that can be acylated to obtain compounds of general formula v.

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

| Abbreviations | |
|---|---|
| Ac | acetyl |
| ACN | acetonitrile |
| AcOH | acetic acid |
| anhyd. | anhydrous |
| aq. | aqueous |
| Bn | benzyl |
| Bu | butyl |
| Boc | tert-butoxycarbonyl |
| BOP | benzotriazol-1-yloxytris-(dimethylamino)-phosphonium hexafluorophosphate |
| DAST | (diethylamino)sulfur trifluoride |
| DCE | dichloroethane |
| DCM | dichloromethane |
| DMAP | dimethylaminopyridine |
| DEA | diethylamine |
| DIPEA | diisopropylethylamine |
| DMF | dimethylformamide |
| DMSO | dimethylsulfoxide |
| EDC | 1-(3-dimethylaminopropyl)-3-ethylcarbodiimide hydrochloride |
| EtOAc | ethyl acetate |
| Et | ethyl |
| EtOH | ethanol |
| H or $H_2$ | hydrogen |
| h, hr or hrs | hour(s) |
| HATU | O-(7-azabenzotriazol-1-yl)-N,N,N',N'-tetramethyluronium hexafluorophosphate |
| HCTU | O-(6-Chlorobenzotriazol-1-yl)-N,N,N',N'-tetramethyluronium hexafluorophosphate |
| hex | hexane |
| i | iso |
| IPA | isopropyl alcohol |
| HOAc | acetic acid |
| HCl | hydrochloric acid |
| HPLC | high pressure liquid chromatography |
| LC | liquid chromatography |
| LCMS | liquid chromatography mass spectrometry |
| M | molar |
| mL or ml | milliliter |
| mM | millimolar |
| Me | methyl |
| MeOH | methanol |
| MHz | megahertz |
| min. | minute(s) |
| mins | minute(s) |
| $M^{+1}$ | $(M + H)^+$ |
| MS | mass spectrometry |
| n or N | normal |
| NBS | n-bromosuccinimide |
| nm | nanometer |
| nM | nanomolar |
| NCS | N-chlorosuccinimide |
| NMP | N-methylpyrrolidine |
| Pd/C | palladium on carbon |
| $PdCl_2(dppf)_2$ | [1,1'-bis(diphenylphosphino)ferrocene]dichloropalladium(II) |
| $Pd(PPh_3)_4$ | tetrakis(triphenylphosphine)palladium |
| Ph | phenyl |
| $PPh_3$ | triphenylphosphine |
| Pr | propyl |
| PSI | pounds per square inch |
| PyBOP | bromotripyrrolidinophosphonium hexafluorophosphate |
| Ret Time | retention time |
| sat. | saturated |
| SFC | supercritical fluid chromatography |
| TEA | triethylamine |
| TFA | trifluoroacetic acid |
| THF | tetrahydrofuran |
| TsCl | 4-toluenesulfonyl chloride |

Analytical LCMS Methods:
Method A: Waters Acquity UPLC BEH C18 (2.1×50 mm), 1.7 micron; Mobile Phase A: 5:95 acetonitrile:water with 10 mM ammonium acetate; Mobile Phase B: 95:5 acetonitrile:water with 10 mM ammonium acetate; Temperature: 50'C; Gradient: 0-100% B over 3 minutes, then a 0.75-minute hold at 100% B; Flow: 1.0 mL/min; Detection: UV at 220 nm.
Method B: Waters Acquity UPLC BEH C18 (2.1×50 mm), 1.7 micron; Mobile Phase A: 5:95 acetonitrile:water with 0.1% trifluoroacetic acid; Mobile Phase B: 95:5 acetonitrile:water with 0.1% trifluoroacetic acid; Temperature: 50'C; Gradient: 0-100% B over 3 minutes, then a 0.75-minute hold at 100% B; Flow: 1.0 mL/min; Detection: UV at 220 nm.
Method C: Waters Acquity UPLC BEH C18 (2.1×50 mm), 1.7 micron; Mobile Phase A=100% water with 0.05% TFA; Mobile Phase B=100% acetonitrile with 0.05% TFA; Gradient=2-98% B over 1 minute, then a 0.5-minute hold at 98% B; Flow rate: 0.8 mL/min; Detection: UV at 220 nm.

Scheme 1

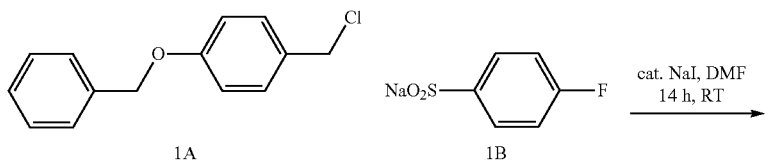

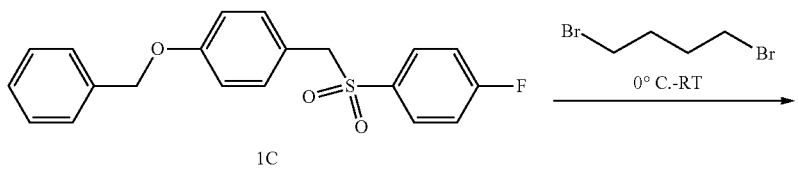

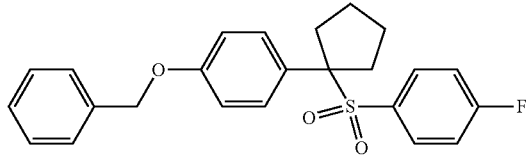

Example 1

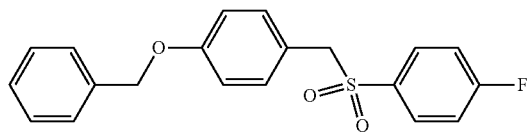

To a 40 mL vial was added 1-(benzyloxy)-4-(chloromethyl)benzene (0.931 g, 4 mmol), sodium 4-fluorobenzenesulfinate (1.020 g, 5.60 mmol), sodium iodide (0.030 g, 0.200 mmol) and anhydrous DMF (6 mL). The resulting reaction mixture was stirred at room temperature for 14 h. An aliquot of the reaction mixture was diluted with methanol and analyzed by LCMS to observe complete disappearance of starting material 1A. To the reaction mixture was added water and stirred. The resulting suspension was filtered. The white residue was washed with water and dried under suction. Obtained 1-(benzyloxy)-4-(((4-fluorophenyl)sulfonyl)methyl)benzene 1C (1.31 g, 3.68 mmol, 92% yield) as a white powder.

LCMS: m/z 379.1 (M+Na), 197.2 (benzylic cation) rt 1.06 min, Method C. $^1$H NMR (DMSO-d$_6$) δ: 7.69-7.77 (m, 2H), 7.30-7.45 (m, 7H), 7.02-7.12 (m, 2H), 6.89-6.97 (m, 2H), 5.07 (s, 2H), 4.60 (s, 2H).

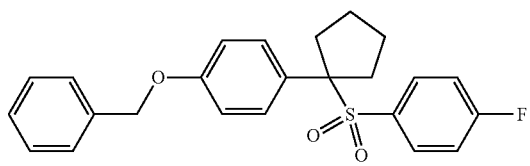 [SMILES: O=S(=O)(c1ccc(F)cc1)C1(c2ccc(OCc3ccccc3)cc2)CCCC1]

Example 1

To a flask was added crude 1-(benzyloxy)-4-(((4-fluorophenyl)sulfonyl) methyl)benzene 1C (1.318 g, 3.70 mmol), DMF (20 mL), 1,4-dibromobutane (1.198 g, 5.55 mmol) and cooled in an ice water bath. To the reaction mixture was portion wise added a 60% dispersion of NaH (0.444 g, 11.09 mmol) in mineral oil, waiting for gas evolution to subside between additions. The reaction mixture was stirred at 0° C. for 1 h and then gradually allowed to warm up to 15° C. An aliquot of the reaction mixture was quenched with methanol and analyzed by LCMS to observe mass corresponding to M-BnOPh. The reaction mixture was quenched with water and aqueous ammonium chloride. The reaction mixture was diluted with ethyl acetate (100 mL), washed with water (3×100 mL) and brine (lx 100 mL). The organic phase was dried over sodium sulfate and filtered through a pad of silica gel. The filtrate was concentrated and purified by silica gel chromatography using 0-10% EtOAc in hexanes. Obtained 1-(benzyloxy)-4-(1-((4-fluorophenyl)sulfonyl)cyclopentyl) benzene Example 1 (836 mg, 1.83 mmol, 49% yield) as a colorless crystalline solid. LCMS: 251 (tertiary benzylic cation), rt 1.16 min, Method C. $^1$H NMR (CHLOROFORM-d) δ: 7.32-7.48 (m, 5H), 7.23-7.29 (m, 2H) [overlapping with CHCl3 peak], 7.05-7.15 (m, 2H), 6.89-6.99 (m, 2H), 6.78-6.87 (m, 2H), 5.08 (s, 2H), 2.68-2.85 (m, 2H), 2.19-2.35 (m, 2H), 1.94-2.11 (m, 2H), 1.62-1.76 (m, 2H).

Scheme 2 (Racemic route)

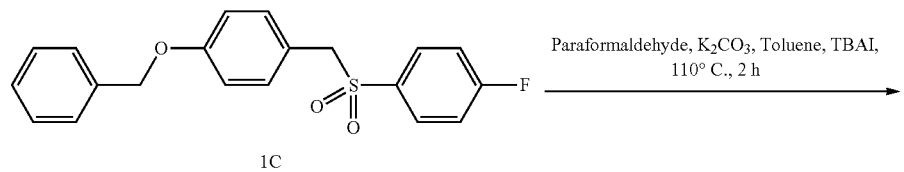

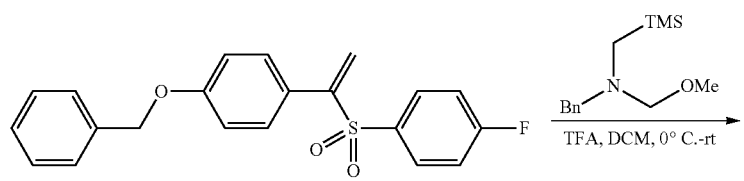

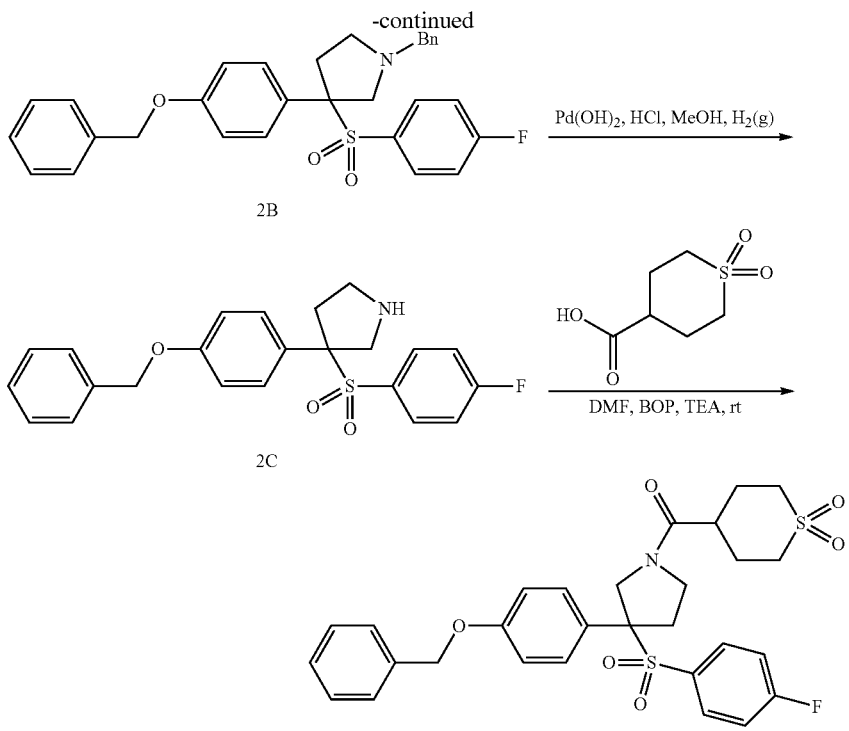

Example 2

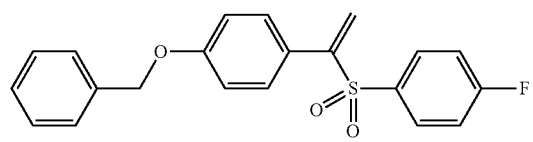

2A

To a solution of 1-(benzyloxy)-4-(((4-fluorophenyl)sulfonyl)methyl)benzene 1C (1.0 g, 2.81 mmol) in toluene (20 mL) was added paraformaldehyde (0.632 g, 7.01 mmol), potassium carbonate (1.163 g, 8.42 mmol) and tetrabutylammonium iodide (10.36 mg, 0.028 mmol). The reaction mixture was heated at 110° C. for 3 h. The reaction mixture was diluted with EtOAc and washed with water then with brine. The organic phase was dried with MgSO₄ and concentrated. The resulting residue was purified by silica gel chromatography using 0-30% EtOAc in hexanes to yield 1-(benzyloxy)-4-(1-((4-fluorophenyl)sulfonyl)vinyl)benzene 2A (0.93 g, 2.52 mmol, 90% yield). $^1$H NMR (400 MHz, DMSO-$d_6$) δ 7.76 (dd, J=5.17, 8.91 Hz, 2H), 7.36-7.48 (m, 5H), 7.26-7.36 (m, 4H), 6.98 (d, J=8.80 Hz, 2H), 6.48 (d, J=0.66 Hz, 1H), 6.21 (d, J=0.70 Hz, 1H), 5.09 (s, 2H).

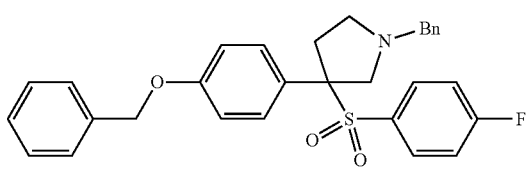

2B

To a solution of 1-(benzyloxy)-4-(1-((4-fluorophenyl)sulfonyl)vinyl)benzene 2A (0.90 g, 2.443 mmol), N-benzyl-1-methoxy-N-((trimethylsilyl)methyl)methanamine (0.580 g, 2.44 mmol) in DCM (15 mL) at 0° C. was added a solution of TFA (0.094 mL, 1.22 mmol) in DCM (2 mL) dropwise. The reaction mixture was stirred at 0° C. for 30 min then at rt for 16 h. LCMS indicated presence of desired pdt as well as SM. The reaction mixture diluted with EtOAc, washed with water then with brine. The organic phase was dried with MgSO₄ and concentrated. The resulting yellow oil was purified by silica gel chromatography using 0-50% EtOAc in hexanes to give 1-benzyl-3-(4-(benzyloxy)phenyl)-3-((4-fluorophenyl)sulfonyl)pyrrolidine 2B (0.42 g, 0.84 mmol, 34% yield) and recovered 1-(benzyloxy)-4-(1-((4-fluorophenyl)sulfonyl)vinyl)benzene 2A (0.29 g, 0.79 mmol, 32% yield). $^1$H NMR (400 MHz, CHLOROFORM-d) δ 7.40-7.48 (m, 4H), 7.36-7.39 (m, 1H), 7.30-7.35 (m, 4H), 7.28 (s, 2H), 7.24-7.27 (m, 1H), 7.01-7.08 (m, 2H), 6.91-7.00 (m, 2H), 6.80-6.88 (m, 2H), 5.08 (s, 2H), 3.60-3.78 (m, 3H), 3.21 (d, J=10.78 Hz, 1H), 2.88-3.01 (m, 2H), 2.73 (m, 1H), 2.43-2.57 (m, 1H). LCMS m/z=502.2 (M+1); rt 0.88 min; Method C.

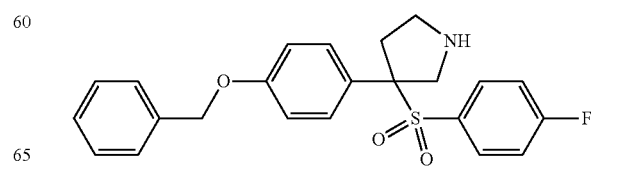

2C

To a solution of 1-benzyl-3-(4-(benzyloxy)phenyl)-3-((4-fluorophenyl) sulfonyl)pyrrolidine 2B (0.64 g, 1.27 mmol) in MeOH (25 mL) cooled in ice-water bath, was added 1 N HCl (1.5 ml, 1.5 mmol) and exchanged vacuum and nitrogen a few times followed by addition of Pearlman's Catalyst (0.27 g, 0.38 mmol) under nitrogen. Hydrogenated under a balloon of H2 overnight allowing the reaction mixture to gradually warm up to rt. LCMS indicated presence of desired product. To the reaction mixture was added Celite and DCM. The resulting suspension was filtered. The filtrate was concentrated to afford the desired product 2C (456 mg, 86% crude yld.) as an off white solid. This crude product was used as such in the next step. LCMS: m/z 411.8; rt 1.62 min; Method A.

Example 2

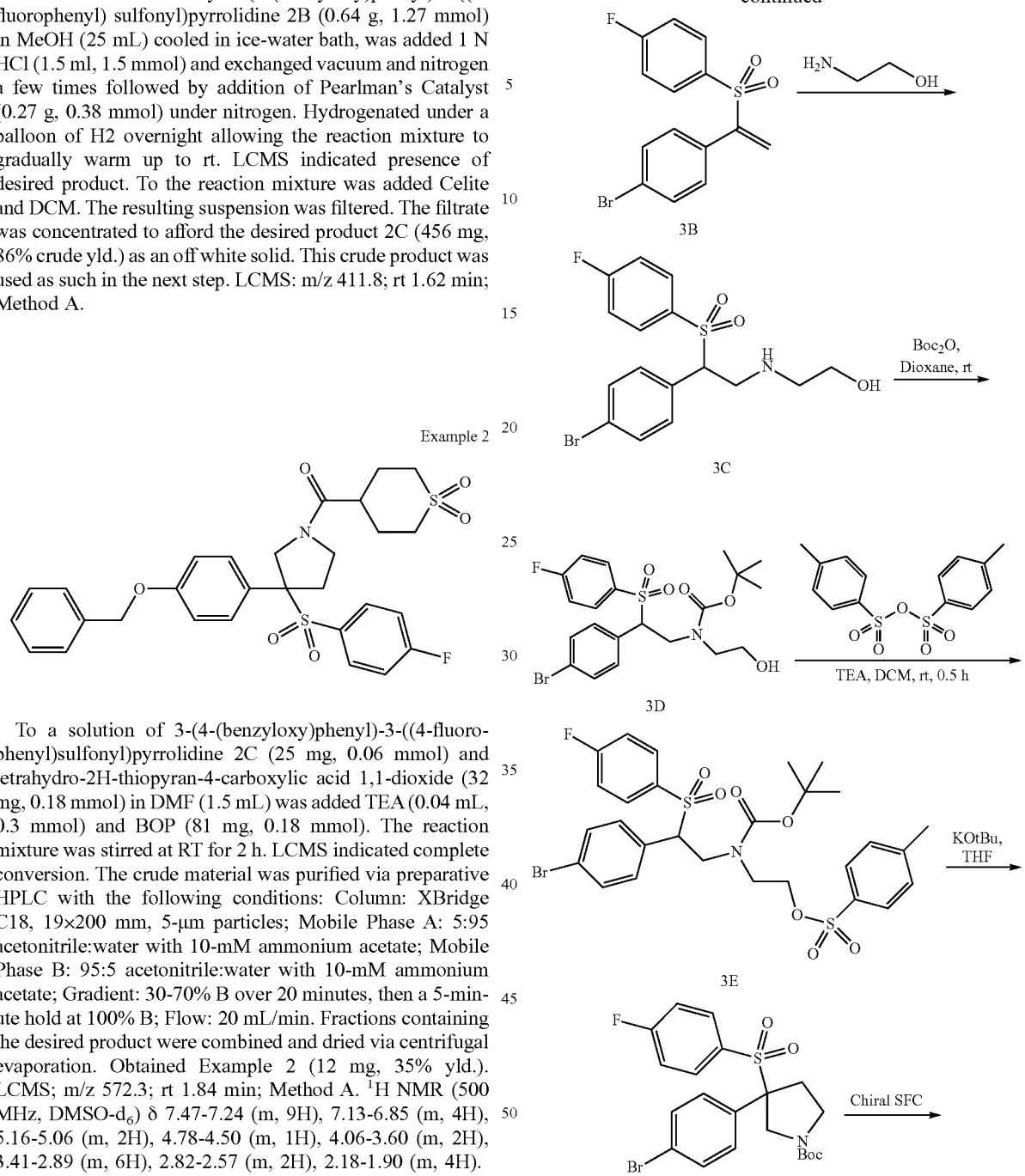

To a solution of 3-(4-(benzyloxy)phenyl)-3-((4-fluorophenyl)sulfonyl)pyrrolidine 2C (25 mg, 0.06 mmol) and tetrahydro-2H-thiopyran-4-carboxylic acid 1,1-dioxide (32 mg, 0.18 mmol) in DMF (1.5 mL) was added TEA (0.04 mL, 0.3 mmol) and BOP (81 mg, 0.18 mmol). The reaction mixture was stirred at RT for 2 h. LCMS indicated complete conversion. The crude material was purified via preparative HPLC with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 minutes, then a 5-minute hold at 100% B; Flow: 20 mL/min. Fractions containing the desired product were combined and dried via centrifugal evaporation. Obtained Example 2 (12 mg, 35% yld.). LCMS; m/z 572.3; rt 1.84 min; Method A. $^1$H NMR (500 MHz, DMSO-$d_6$) δ 7.47-7.24 (m, 9H), 7.13-6.85 (m, 4H), 5.16-5.06 (m, 2H), 4.78-4.50 (m, 1H), 4.06-3.60 (m, 2H), 3.41-2.89 (m, 6H), 2.82-2.57 (m, 2H), 2.18-1.90 (m, 4H).

Scheme 3

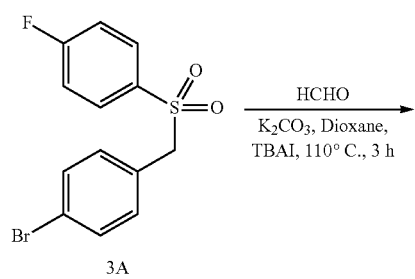

3A

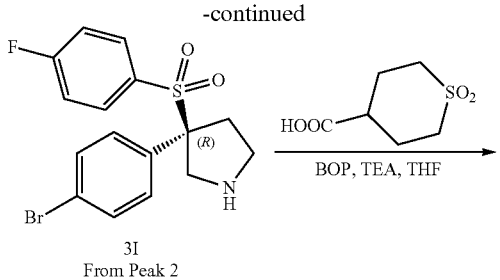

3I
From Peak 2

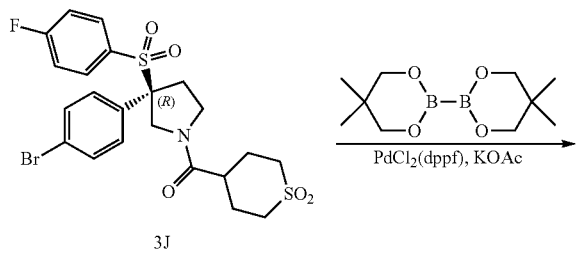

3J

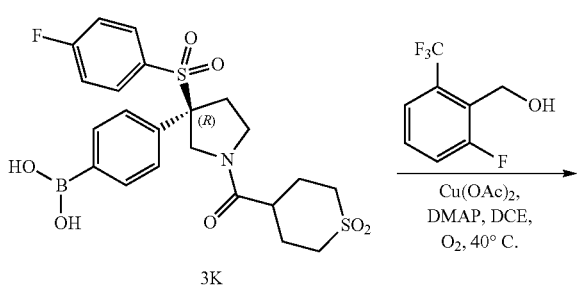

3K

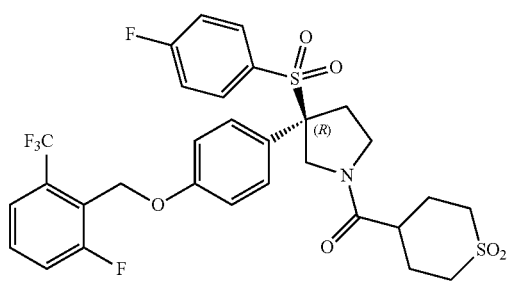

Example 3

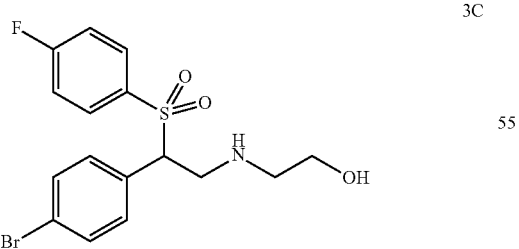

3C

To a solution of 1-bromo-4-(((4-fluorophenyl)sulfonyl) methyl)benzene 3A (4.23 g, 12.85 mmol) in dioxane (125 mL) was added paraformaldehyde (4.63 g, 51.4 mmol), potassium carbonate (5.33 g, 38.5 mmol) and tetrabutylammonium iodide (0.237 g, 0.642 mmol). The reaction mixture was heated at 110° C. for 3 h. LCMS indicated complete conversion to vinyl intermediate 3B. The reaction mixture was diluted with EtOAc and filtered over Celite. The solvent was concentrated to give crude 1-bromo-4-(1-((4-fluorophenyl)sulfonyl)vinyl)benzene 3B which was taken to the next step without further purification. The crude 1-bromo-4-(1-((4-fluorophenyl)sulfonyl)vinyl)benzene 3B was suspended in THF (100 mL) and 2-aminoethanol (1.177 g, 19.27 mmol) was added. The reaction mixture was stirred at rt overnight. Obtained intermediate amine 3C (5.17 g, 51% yld.). LCMS: m/z 401.9, 403.9 (M+1 and M+3); rt 0.69 min; Method C.

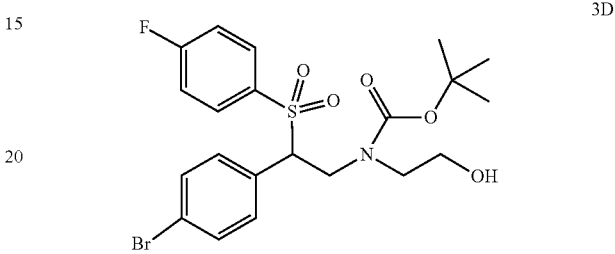

3D

A to a solution of 2-((2-(4-bromophenyl)-2-((4-fluorophenyl)sulfonyl) ethyl)amino)ethanol 3C (2.6 g, 6.46 mmol) in was added TEA (2.70 ml, 19.39 mmol) and di-tert-butyl dicarbonate (1.411 g, 6.46 mmol). The reaction mixture was stirred at rt 1.5 h. LCMS indicated complete conversion. The reaction mixture was concentrated and purified by silica gel chromatography using 0-100% EtOAc in hexanes. Obtained tert-butyl tert-butyl (2-(4-bromophenyl)-2-((4-fluorophenyl)sulfonyl)ethyl)(2-hydroxyethyl)carbamate 3D (3.0 g, 5.97 mmol, 92% yield). LCMS m/z 401.9, 403.9 (M-Boc, one Br); rt 1.00 min; Method C. $^1$H NMR (DMSO-d$_6$) δ: 7.75 (br d, J=4.2 Hz, 2H), 7.53 (br dd, J=18.6, 8.0 Hz, 2H), 7.43 (t, J=8.8 Hz, 2H), 7.18-7.31 (m, 2H), 4.85-5.15 (m, 1H), 4.67 (br s, 1H), 3.82-4.17 (m, 1H), 3.24-3.44 (m, 3H), 2.85-3.11 (m, 2H), 1.23 (s, 9H).

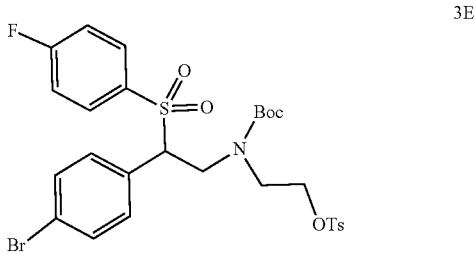 [SMILES: Cc1ccc(S(=O)(=O)OCCN(CC(c2ccc(Br)cc2)S(=O)(=O)c2ccc(F)cc2)C(=O)OC(C)(C)C)cc1]

3E

To a solution of tert-butyl (2-(4-bromophenyl)-2-((4-fluorophenyl)sulfonyl)ethyl)(2-hydroxyethyl)carbamate 3D (2.97 g, 5.91 mmol) in DCM (200 mL) was added TEA (4.1 mL, 29.6 mmol) and then 4-methylbenzenesulfonic anhydride (2.31 g, 7.1 mmol) was added in portions. The reaction mixture was stirred at rt of 1 h. LCMS indicated complete conversion. The reaction mixture was diluted with DCM, washed with sat K$_2$HPO$_4$, then with brine, dried and purified by silica gel chromatography using 0-100% EtOAc in hexanes to give 2-((2-(4-bromophenyl)-2-((4-fluorophenyl) sulfonyl)ethyl)(tert-butoxycarbonyl)amino)ethyl 4-methylbenzenesulfonate 3E (3.8 g, 5.79 mmol, 98% yield). LCMS m/z 555.8, 557.8 (M-Boc); rt 1.16 min; Method C.

3F

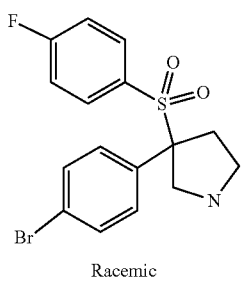

Racemic

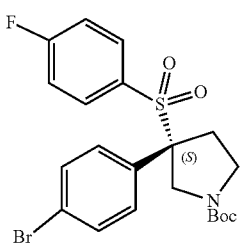

Peak 1
Stereochem determined
by X-ray of Mosher amide.

3H

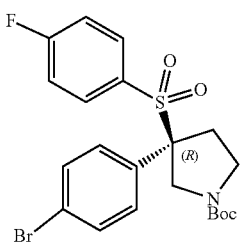

Peak 2

To a solution of 2-((2-(4-bromophenyl)-2-((4-fluorophenyl)sulfonyl)ethyl)(tert-butoxycarbonyl)amino)ethyl 4-methylbenzenesulfonate 3E (3.8 g, 5.79 mmol) in THF (200 mL) cooled to −10° C. potassium tert-butoxide (5.2 ml, 5.2 mmol) was added dropwise and the reaction warmed up to rt over 30 min. LCMS indicated complete conversion. The reaction mixture was diluted with EtOAc, washed with saturated aqueous $NH_4Cl$. The organics phase was washed with brine, dried over $MgSO_4$ and concentrated. The crude product was purified by silica gel chromatography using 0-70% EtOAc in hexanes to yield tert-butyl 3-(4-bromophenyl)-3-((4-fluorophenyl)sulfonyl)pyrrolidine-1-carboxylate 3F (1.3 g, 2.68 mmol, 46% yield). $^1$H NMR (DMSO-$d_6$) δ: 7.46-7.60 (m, 4H), 7.33-7.45 (m, 2H), 7.07 (d, J=8.6 Hz, 2H), 4.41-4.55 (m, 1H), 3.63-3.82 (m, 1H), 3.23-3.40 (m, 2H) integration obscured by water resonance, 2.89-3.09 (m, 1H), 1.33-1.53 (m, 9H). This racemic mixture was resolved by preparative chiral SFC (Column: Lux Cellulose-4 (5×25 cm, 5 μm, #548090); BPR pressure: 100 bars; Temperature: 35° C.; Flow rate: 250 mL/min; Mobile Phase: CO2/MeOH (70/30); Detector Wavelength: 220 nm; Separation Program: Stack injection) to obtain peak 1 (550 mg, S enantiomer) and peak 2 (470 mg, R enantiomer). The fraction corresponding to peak 1 was concentrated. The absolute configuration was determined to be S (Mosher amide followed by X-ray). Therefore the absolute configuration of peak 2 was assigned as R.

3J

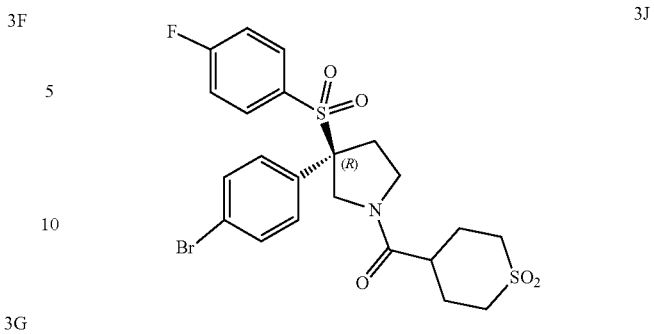

To a solution of tert-butyl (R)-3-(4-bromophenyl)-3-((4-fluorophenyl)sulfonyl)pyrrolidine-1-carboxylate 3H (225 mg, 0.465 mmol) in DCM (4 mL) was added 1 N HCl (1 mL). The reaction mixture was stirred at rt for 30 min then concentrated. The resulting residue was dissolved in DCM, stirred with wet $K_2CO_3$, filtered and concentrated. The resulting amine 31 was dissolved in THF (4 mL) and treated with tetrahydro-2H-thiopyran-4-carboxylic acid 1,1-dioxide (124 mg, 0.697 mmol), BOP (308 mg, 0.697 mmol) and TEA (0.194 mL, 1.394 mmol). The resulting reaction mixture was stirred at rt for 1 h. The reaction mixture was concentrated and purified by silica gel chromatography using 0-100% EtOAc in DCM to yield (R)-(3-(4-bromophenyl)-3-((4-fluorophenyl)sulfonyl)pyrrolidin-1-yl)(1,1-dioxidotetrahydro-2H-thiopyran-4-yl)methanone 3J (0.22 g, 0.404 mmol, 87% yield).

3K

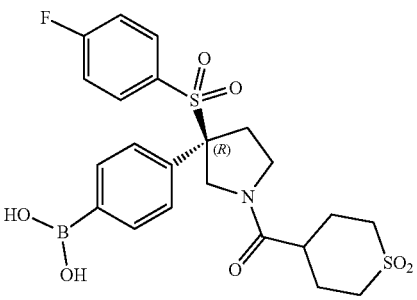

A solution of (R)-(3-(4-bromophenyl)-3-((4-fluorophenyl)sulfonyl)pyrrolidin-1-yl)(1,1-dioxidotetrahydro-2H-thiopyran-4-yl)methanone 3J (0.22 g, 0.40 mmol), potassium acetate (0.119 g, 1.21 mmol), PdCl2(dppf)-$CH_2Cl_2$ adduct (0.033 g, 0.040 mmol) and 5,5,5',5'-tetramethyl-2,2'-bi(1,3,2-dioxaborinane) (0.137 g, 0.606 mmol) in Acetonitrile (8.08 ml) was purged with argon & heated at reflux for 3 h. LCMS indicated the formation of boronic acid 3K. The reaction mixture was cooled to room temperature, diluted with ethyl acetate (10 mL) and filtered through Celite. The filtrate was concentrated under reduced pressure and purified by silica gel chromatography using 0-8% MeOH in DCM. Obtained (R)-(4-(1-(1,1-dioxidotetrahydro-2H-thiopyran-4-carbonyl)-3-((4-fluorophenyl)sulfonyl)pyrrolidin-3-yl)phenyl)boronic acid 3K (180 mg, 0.35 mmol, 87% yield). LCMS: m/z 510.0 (M+1); rt 0.64 min; Method C.

Example 3

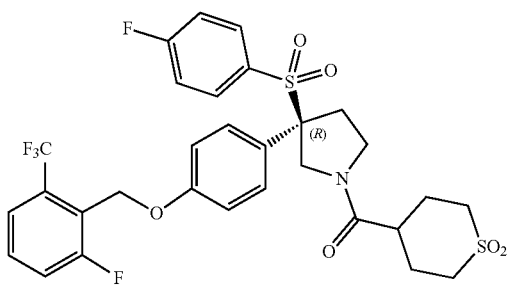

To a solution of (R)-(4-(1-(1,1-dioxidotetrahydro-2H-thiopyran-4-carbonyl)-3-((4-fluorophenyl)sulfonyl)pyrrolidin-3-yl)phenyl)boronic acid 3K (20 mg, 0.039 mmol), DMAP (4.80 mg, 0.039 mmol), copper (II) acetate (14.26 mg, 0.079 mmol) and (2-fluoro-6-(trifluoromethyl)phenyl) methanol (0.069 mmol) in DCE (2 mL) was added 200 mg 4 A molecular sieves. The reaction mixture was stirred bubbled with oxygen (g), capped and stirred overnight at 40° C. An aliquot of the reaction mixture was analyzed by LCMS to ensure complete conversion. The reaction mixture was filtered. The filtrate was washed with saturated aq. NH4Cl. The organic layer was dried and concentrated. The residue was purified by reverse phase TPLC. Obtained Example 3. The crude material was purified via preparative LC. The yield of the product was 5.6 mg. LCMS m/z 658.01; rt 2.01 min; Method B. $^1$H NMR (DMSO-d$_6$) δ: 7.60-7.83 (m, 3H), 7.49 (br d, J=5.1 Hz, 1H), 7.24-7.41 (m, 3H), 7.12 (br d, J=8.2 Hz, 1H), 6.88-7.05 (m, 3H), 5.14 (br d, J=7.1 Hz, 2H), 4.46-4.81 (m, 1H), 2.57-3.44 (m, 8H), 1.85-2.17 (m, 4H).

The above synthetic sequence allowed for variation of benzyl ether late in the synthesis. This sequence of reactions can be switched to where the SM aryl bromide # was converted to the benzyl ether, followed by Boc removal and amide bond formation. This allowed for amide variations late in the synthesis.

The following examples were synthesized according to the procedures described above.

| Example | Structure & Name | Analytical Data | Procedure Analogous to Example No. |
|---|---|---|---|
| 4 | 1-[1-(4-fluorobenzenesulfonyl)cyclopentyl]-4-(2-phenylethoxy)benzene | Method C: rt = 1.16 min; Obs. Adduct: [M + Na]; Obs. Mass: 447.0; | 1 |
| 5 | 1-(benzyloxy)-4-[1-(3-chlorobenzenesulfonyl)cyclopentyl]benzene | Method C: rt = 1.22 min; Obs. Adduct: [M − SO$_2$Ar]; Obs. Mass: 251.2; | 1 |
| 6 | 1-[1-(benzenesulfonyl)cyclopentyl]-4-(benzyloxy)benzene | Method A: rt = 2.42 min; Obs. Adduct: [M + NH4]; Obs. Mass: 410.14; Method B: rt = 2.42 min; Obs. Adduct: [M + Na]; Obs. Mass: 415.07 | 1 |

-continued

| Example | Structure & Name | Analytical Data | Procedure Analogous to Example No. |
|---|---|---|---|
| 7 | 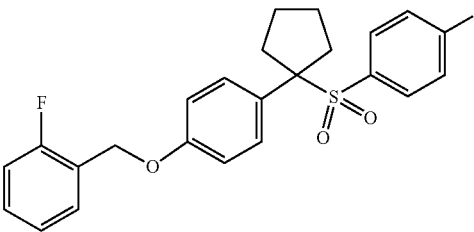<br>1-[1-(4-fluorobenzenesulfonyl)cyclopentyl]-4-[(2-fluorophenyl)methoxy]benzene | Method B: rt = 2.57 min;<br>Method A: rt = 2.67 min; | 1 |
| 8 | 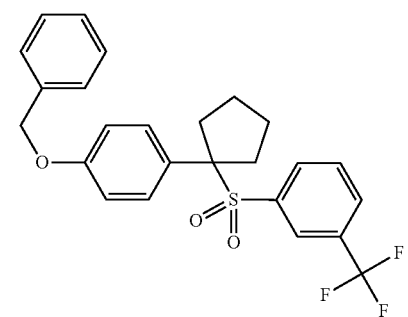<br>1-(benzyloxy)-4-{1-[3-(trifluoromethyl)benzenesulfonyl]cyclopentyl}benzene | Method B: rt = 2.53 min;<br>Obs. Adduct: [M + Na];<br>Obs. Mass: 483;<br>Method A: rt = 2.61 min;<br>Obs. Adduct: [M + 2H]2+/2;<br>Obs. Mass: 231.23 | 1 |
| 9 | 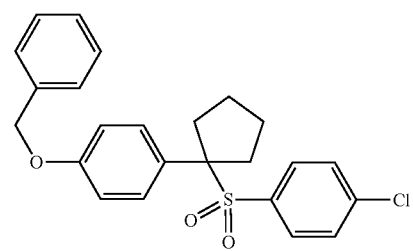<br>1-(benzyloxy)-4-[1-(4-chlorobenzenesulfonyl)cyclopentyl]benzene | Method A: rt = 2.63 min;<br>Obs. Adduct: [M + NH4];<br>Obs. Mass: 444.18;<br>Method B: rt = 2.63 min;<br>Obs. Adduct: [M + Na];<br>Obs. Mass: 449.09 | 1 |
| 10 | 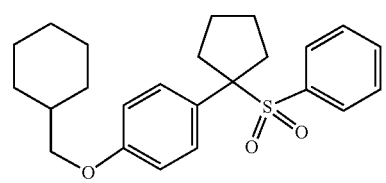<br>1-[1-(benzenesulfonyl)cyclopentyl]-4-(cyclohexylmethoxy)benzene | Method A: rt = 2.79 min;<br>Obs. Adduct: [M + NH4];<br>Obs. Mass: 416.15;<br>Method B: rt = 2.78 min;<br>Obs. Adduct: [M + Na];<br>Obs. Mass: 421.09 | 1 |
| 11 | 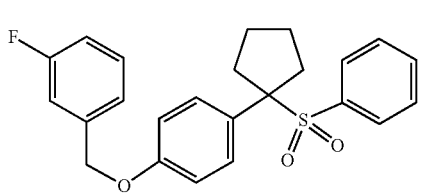<br>1-[1-(benzenesulfonyl)cyclopentyl]-4-[(3-fluorophenyl)methoxy]benzene | Method A: rt = 2.37 min;<br>Obs. Adduct: [M + NH4];<br>Obs. Mass: 427.96;<br>Method B: rt = 2.42 min;<br>Obs. Adduct: [M + NH4];<br>Obs. Mass: 428.16 | 1 |

-continued

| Example | Structure & Name | Analytical Data | Procedure Analogous to Example No. |
|---|---|---|---|
| 12 | 1-[1-(benzenesulfonyl)cyclopentyl]-4-[(4-fluorophenyl)methoxy]benzene | Method A: rt = 2.36 min; Obs. Adduct: [M + NH4]; Obs. Mass: 428.26; Method B: rt = 2.41 min; Obs. Adduct: [M + NH4]; Obs. Mass: 428.06 | 1 |
| 13 | 1-[1-(benzenesulfony)cyclopentyl]-4-[(2-fluorophenyl)methoxy]benzene | Method A: rt = 2.37 min; Obs. Adduct: [M + NH4]; Obs. Mass: 427.86; Method B: rt = 2.41 min; Obs. Adduct: [M + Na]; Obs. Mass: 433.08 | 1 |
| 14 | 1-[1-(benzenesulfonyl)cyclopentyl]-4-(2-cyclopropylethoxy)benzene | Method A: rt = 2.46 min; Method B: rt = 2.46 min; Obs. Adduct: [M + Na]; Obs. Mass: 393.03 | 1 |
| 15 | 1-{3-[4-(benzyloxy)pheny]-3-(4-fluorobenzenesulfonyl)pyrrolidin-1-yl}-2-(oxan-4-yl)ethan-1-one | Method A: rt = 2.04 min; Obs. Adduct: [M + H]; Obs. Mass: 538.29; Method B: rt = 1.98 min; Obs. Adduct: [M + H]; Obs. Mass: 538.34 | 2 |

-continued

| Example | Structure & Name | Analytical Data | Procedure Analogous to Example No. |
|---|---|---|---|
| 16 | 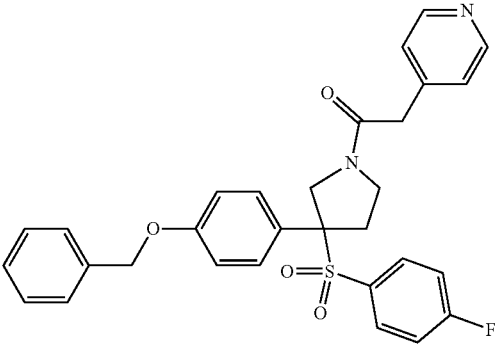<br>1-{3-[4-(benzyloxy)pheny]-3-(4-fluorobenzenesulfonyl)pyrrolidin-1-yl}-2-(pyridin-4-yl)ethan-1-one | Method A: rt = 2.01 min; Obs. Adduct: [M + H]; Obs. Mass: 531.2; Method B: rt = 1.76 min; Obs. Adduct: [M + H]; Obs. Mass: 530.91 | 2 |
| 17 | 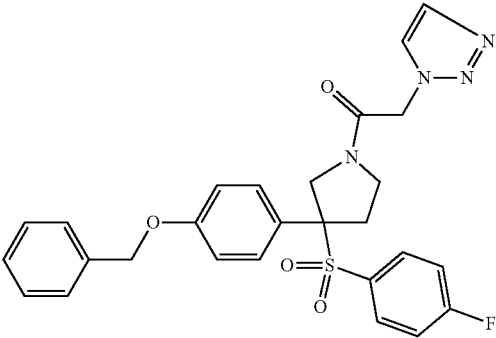<br>1-{3-[4-(benzyloxy)pheny]-3-(4-fluorobenzenesulfonyl)pyrrolidin-1-yl}-2-(1H-1,2,3-triazol-1-yl)ethan-1-one | Method A: rt = 1.99 min; Obs. Adduct: [M + H]; Obs. Mass: 520.92; Method B: rt = 2 min; Obs. Adduct: [M + H]; Obs. Mass: 520.93 | 2 |
| 18 | 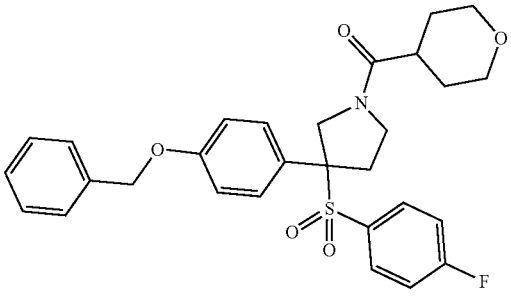<br>3-[4-(benzyloxy)pheny]-3-(4-fluorobenzenesulfonyl)-1-(oxane-4-carbonyl)pyrrolidine | Method A: rt = 1.94 min; Obs. Adduct: [M + H]; Obs. Mass: 524.24; Method B: rt = 1.97 min; Obs. Adduct: [M + H]; Obs. Mass: 524.25 | 2 |

-continued

| Example | Structure & Name | Analytical Data | Procedure Analogous to Example No. |
|---|---|---|---|
| 19 | 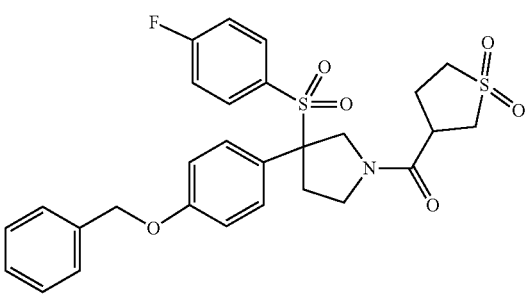<br>3-{3-[4-(benzyloxy)phenyl]-3-(4-(fluorobenzenesulfonyl)pyrrolidine-1-carbonyl}-1$\lambda^6$-thiolane-1,1-dione | Method A: rt = 1.99 min;<br>Obs. Adduct: [M + H];<br>Obs. Mass: 558.17;<br>Method B: rt = 1.88 min;<br>Obs. Adduct: [M + H];<br>Obs. Mass: 558.13 | 2 |
| 20 | 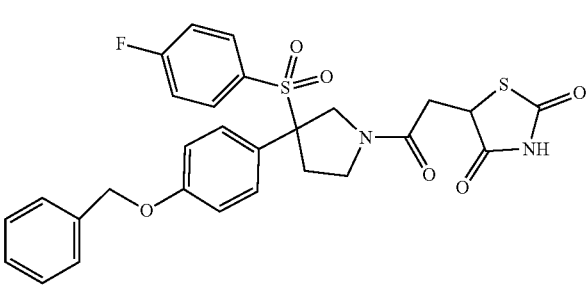 [SMILES: O=C1NC(=O)C(CC(=O)N2CCC(c3ccc(OCc4ccccc4)cc3)(S(=O)(=O)c3ccc(F)cc3)C2)S1]<br>5-(2-{3-[4-(benzyloxy)phenyl]-3-(4-fluorobenzenesulfonyl)pyrrolidin-1-yl}-2-oxoethyl)-1,3-thiazolidine-2,4-dione | Method A: rt = 1.83 min;<br>Obs. Adduct: [M + H];<br>Obs. Mass: 568.98;<br>Method B: rt = 1.9 min;<br>Obs. Adduct: [M + H];<br>Obs. Mass: 569.1 | 2 |
| 21 | 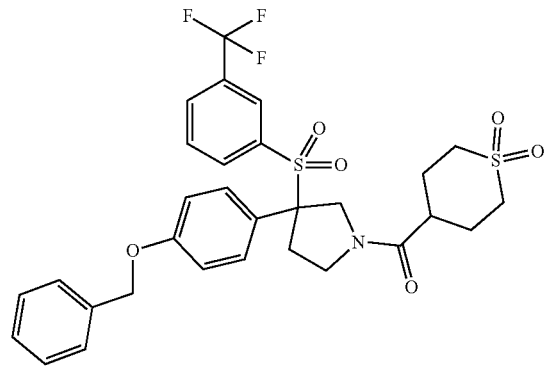<br>4-{3-[4-(benzyloxy)phenyl]-3-[3-(trifluoromethyl)benzenesulfonyl]pyrrolidin-1-carbonyl}-1$\lambda^6$-thiane-1,1-dione | Method A: rt = 2.02 min;<br>Obs. Adduct: [M + H];<br>Obs. Mass: 622.15;<br>Method B: rt = 2 min;<br>Obs. Adduct: [M + H];<br>Obs. Mass: 622.26 | 2 |

-continued

| Example | Structure & Name | Analytical Data | Procedure Analogous to Example No. |
|---|---|---|---|
| 22 | 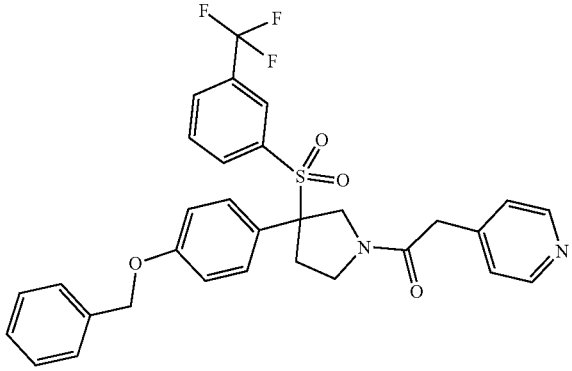<br>1-{3-[4-(benzyloxy)phenyl]-3-[3-(trifluoromethyl)benzenesulfonyl]pyrrolidin-1-yl}-2-(pyridin-4-yl)ethan-1-one | Method A: rt = 2.04 min;<br>Obs. Adduct: [M + H];<br>Obs. Mass: 581.1;<br>Method B: rt = 1.86 min;<br>Obs. Adduct: [M + H];<br>Obs. Mass: 581.12 | 2 |
| 23 | 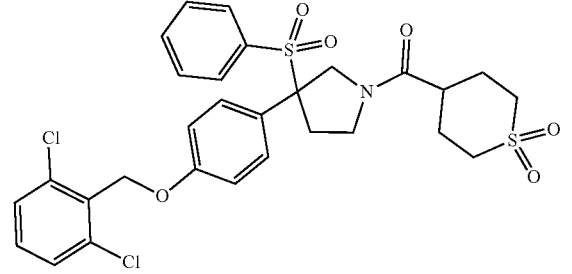<br>4-[3-(benzenesulfonyl)-3-{4-[(2,6-dichlorophenyl)methoxy]phenyl}pyrrolidin-1-carbonyl]-1$\lambda^6$-thiane-1,1-dione | Method A: rt = 2 min;<br>Obs. Adduct: [M + H];<br>Obs. Mass: 621.93;<br>Method B: rt = 1.95 min;<br>Obs. Adduct: [M + H];<br>Obs. Mass: 622.08 | 2 |
| 24 | 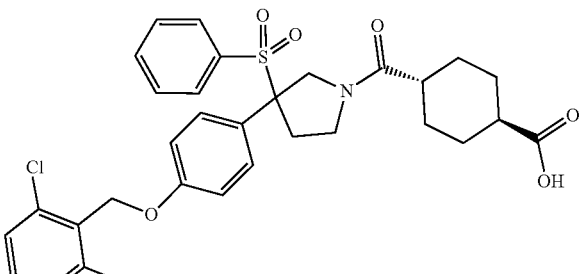<br>(1r,4r)-4-[3-(benzenesulfonyl)-3-{4-[(2,6-dichlorophenyl)methoxy]phenyl}pyrrolidine-1-carbonyl]cyclohexane-1-carboxylic acid | Method A: rt = 1.73 min;<br>Obs. Adduct: [M + H];<br>Obs. Mass: 616.14;<br>Method B: rt = 2.05 min;<br>Obs. Adduct: [M + H];<br>Obs. Mass: 616.18 | 2 |

| Example | Structure & Name | Analytical Data | Procedure Analogous to Example No. |
|---|---|---|---|
| 25 | 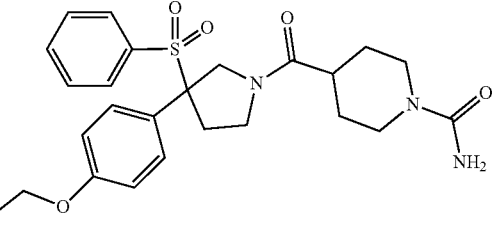<br>4-[3-(benzenesulfonyl)-3-{4-[(2,6-dichlorophenyl)methoxy]phenyl}pyrrolidine-1-carbonyl]piperidine-1-carboxamide | Method A: rt = 1.9 min;<br>Obs. Adduct: [M + H];<br>Obs. Mass: 615.89;<br>Method B: rt = 1.91 min;<br>Obs. Adduct: [M + H];<br>Obs. Mass: 615.92 | 2 |
| 26 | 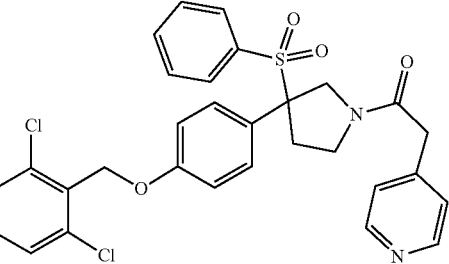<br>1-[3-(benzenesulfonyl)-3-{4-[(2,6-dichlorophenyl)methoxy]phenyl}pyrrolidin-1-yl]-2-(pyridin-4-yl)ethan-1-one | Method A: rt = 2.02 min;<br>Obs. Adduct: [M + H];<br>Obs. Mass: 581.15;<br>Method B: rt = 1.83 min;<br>Obs. Adduct: [M + H];<br>Obs. Mass: 581.14 | 2 |
| 27 | 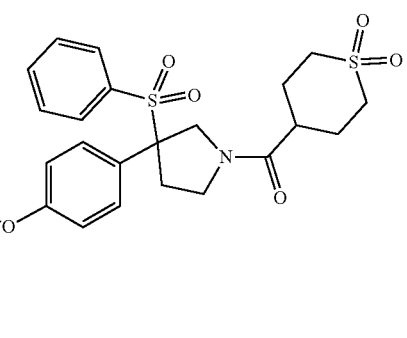<br>4-[3-(benzenesulfonyl)-3-{4-[(2-chloro-3,6-dichlorophenyl)methoxy]phenyl}pyrrolidine-1-carbonyl}-1$\lambda^6$-thiane-1,1-dione | Method B: rt = 1.92 min;<br>Obs. Adduct: [M + H];<br>Obs. Mass: 624.14;<br>Method A: rt = 1.92 min;<br>Obs. Adduct: [M + H];<br>Obs. Mass: 623.9 | 2 |

| Example | Structure & Name | Analytical Data | Procedure Analogous to Example No. |
|---|---|---|---|
| 28 | 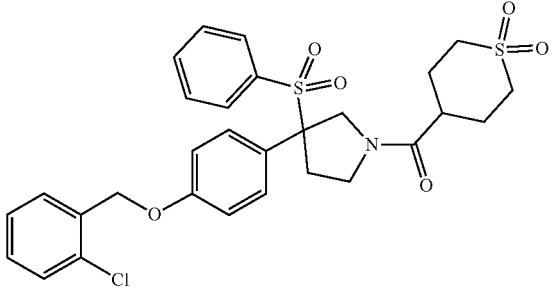<br>4-[3-(benzenesulfonyl)-3-{4-[(2-chlorophenyl)methoxy]phenyl} pyrrolidine-1-carbonyl}-1λ⁶-thiane-1,1-dione | Method A: rt = 1.95 min; Obs. Adduct: [M + H]; Obs. Mass: 588.18; Method B: rt = 1.91 min; Obs. Adduct: [M + H]; Obs. Mass: 588.15 | 2 |
| 29 | 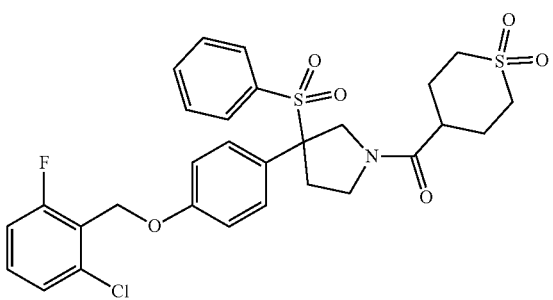<br>4-[3-(benzenesulfonyl)-3-{4-[(2-chloro-6-fluorophenyl) methoxy]phenyl} pyrrolidine-1-carbonyl]-1λ⁶-thiane-1,1-dione | Method B: rt = 1.86 min; Obs. Adduct: [M + H]; Obs. Mass: 606.07; Method A: rt = 1.89 min; Obs. Adduct: [M + H]; Obs. Mass: 606.07 | 2 |
| 30 | 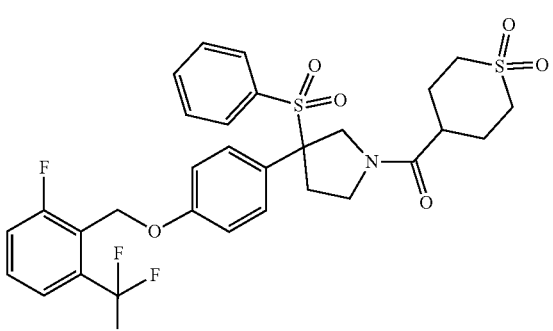<br>4-[3-(benzenesulfonyl)-3-{4-[(2-fluoro-6-(trifluoromethyl) phenyl]methoxy}phenyl) pyrrolidine-1-carbonyl]-1λ⁶-thiane-1,1-dione | Method A: rt = 1.93 min; Obs. Adduct: [M + H]; Obs. Mass: 640.08; Method B: rt = 1.9 min; Obs. Adduct: [M + H]; Obs. Mass: 640.18 | 2 |

-continued

| Example | Structure & Name | Analytical Data | Procedure Analogous to Example No. |
|---|---|---|---|
| 31 | 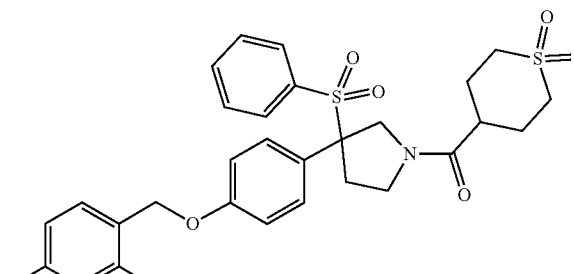<br>4-[3-(benzenesulfonyl)-3-{4-[(2-chloro-4-fluorophenyl)methoxy]phenyl}pyrrolidine-1-carbonyl]-1$\lambda^6$-thiane-1,1-dione | Method A: rt = 1.99 min; Obs. Adduct: [M + H]; Obs. Mass: 605.98; Method B: rt = 1.95 min; Obs. Adduct: [M + H]; Obs. Mass: 606.02 | 2 |
| 32 | 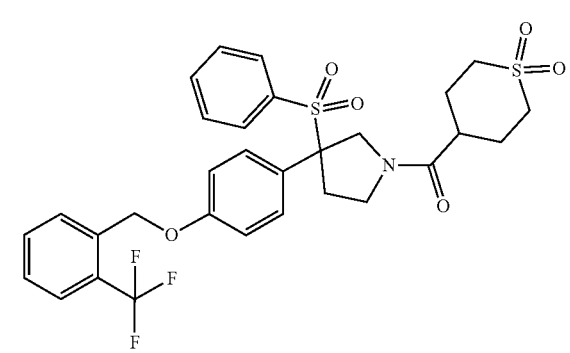<br>4-[3-(benzenesulfonyl)-3-(4-{[2-(trifluoromethyl)phenyl]methoxy}phenyl)pyrrolidine-1-carbonyl]-1$\lambda^6$-thiane-1,1-dione | Method A: rt = 1.99 min; Obs. Adduct: [M + H]; Obs. Mass: 622.24; Method B: rt = 1.96 min; Obs. Adduct: [M + H]; Obs. Mass: 622.03 | 2 |
| 33 | 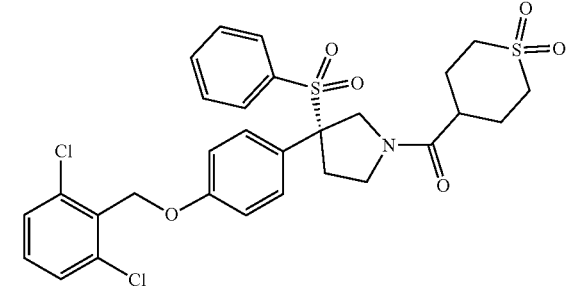<br>4-[(3R)-3-(benzenesulfonyl)-3-{4-[(2,6-dichlorophenyl)methoxy]phenyl}pyrrolidine-1-carbonyl]-1$\lambda^6$-thiane-1,1-dione | Method A: rt = 1.99 min; Obs. Adduct: [M + H]; Obs. Mass: 622; Method B: rt = 1.93 min; Obs. Adduct: [M + H]; Obs. Mass: 621.95 | 3 |

-continued

| Example | Structure & Name | Analytical Data | Procedure Analogous to Example No. |
|---|---|---|---|
| 34 | (1r,4r)-4-[(3R)-3-(benzenesulfonyl)-3-{4-[(2,6-dichlorophenyl)methoxy]phenyl}pyrrolidine-1-carbonyl]-cyclohexane-1-carboxylic acid | Method A: rt = 1.69 min; Obs. Adduct: [M + H]; Obs. Mass: 615.97; Method B: rt = 1.99 min; Obs. Adduct: [M + H]; Obs. Mass: 615.97 | 3 |
| 35 | (1r,4r)-4-[(3R)-3-{4-[(2,6-dichlorophenyl)methoxy]phenyl}-3-(4-fluorobenzenesulfonyl)-pyrrolidine-1-carbonyl]-cyclohexane-1-carboxylic acid | Method A: rt = 1.73 min; Obs. Adduct: [M + H]; Obs. Mass: 634; Method B: rt = 2.07 min; Obs. Adduct: [M + H]; Obs. Mass: 634.08 | 3 |
| 36 | 4-[(3R)-3-{4-[(2,6-dichlorophenyl)methoxy]phenyl}-3-(4-fluorobenzenesulfonyl)-pyrrolidine-1-carbonyl]-1$\lambda^6$-thiane-1,1-dione | Method A: rt = 2.04 min; Obs. Adduct: [M + H]; Obs. Mass: 640.12; Method B: rt = 2.03 min; Obs. Adduct: [M + H]; Obs. Mass: 640 | 3 |

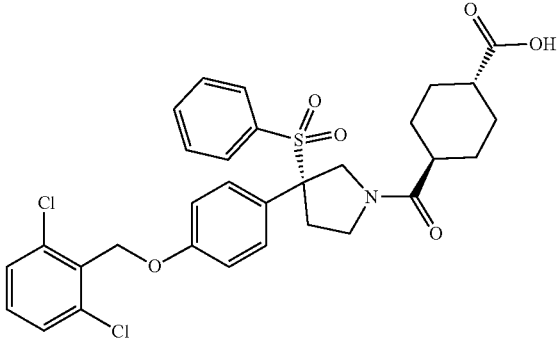

| Example | Structure & Name | Analytical Data | Procedure Analogous to Example No. |
|---|---|---|---|
| 37 | 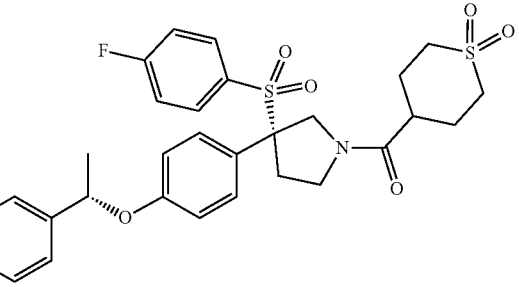<br>4-[(3R)-3-{4-fluorobenzenesulfonyl)-3-{4-[(1S)-1-phenylethoxy]phenyl}pyrrolidine-1-carbonyl]-1$\lambda^6$-thiane-1,1-dione | Method A: rt = 1.95 min;<br>Obs. Adduct: [M + H];<br>Obs. Mass: 586.12;<br>Method B: rt = 1.92 min;<br>Obs. Adduct: [M + H];<br>Obs. Mass: 586.12 | 3 |
| 38 | 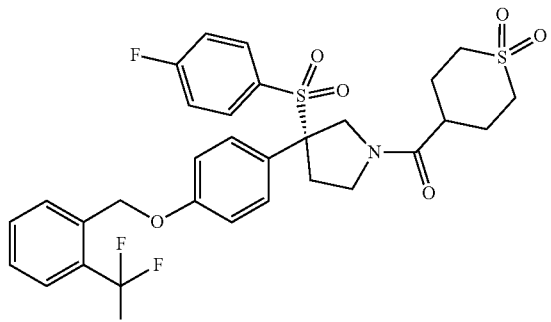<br>4-[(3R)-3-(4-fluorobenzenesulfonyl)-3-(4-{[2-(trifluoromethyl)phenyl]methoxy}phenyl)pyrrolidine-1-carbonyl]-1$\lambda^6$-thiane-1,1-dione | Method A: rt = 2.03 min;<br>Obs. Adduct: [M + H];<br>Obs. Mass: 640.34;<br>Method B: rt = 2.01 min;<br>Obs. Adduct: [M + H];<br>Obs. Mass: 640.34 | 3 |
| 39 | 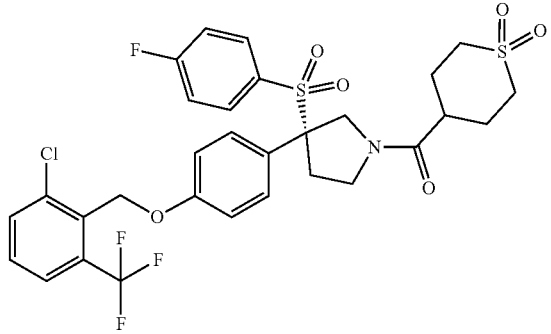<br>4-[(3R)-3-(4-{[2-chloro-6-(trifluoromethyl)phenyl]methoxy}phenyl)-3-(4-fluorobenzenesulfonyl)pyrrolidine-1-carbonyl]-1$\lambda^6$-thiane-1,1-dione | Method A: rt = 2.06 min;<br>Obs. Adduct: [M + H];<br>Obs. Mass: 674.04;<br>Method B: rt = 2.03 min;<br>Obs. Adduct: [M + H];<br>Obs. Mass: 674.29 | 3 |

| Example | Structure & Name | Analytical Data | Procedure Analogous to Example No. |
|---|---|---|---|
| 40 | 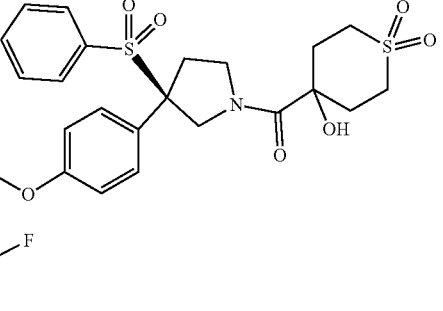<br>4-[(3R)-3-(benzenesulfonyl)-3-(4-{[2-(fluoro-6-(trifluoromethyl)phenyl]methoxy}phenyl)pyrrolidine-1-carbonyl]-4-hydroxy-1λ⁶-thiane-1,1-dione | Method A: rt = 1.92 min; Obs. Adduct: [M + H]; Obs. Mass: 656.06; Method B: rt = 1.9 min; Obs. Adduct: [M + H]; Obs. Mass: 655.97 | 3 |
| 41 | 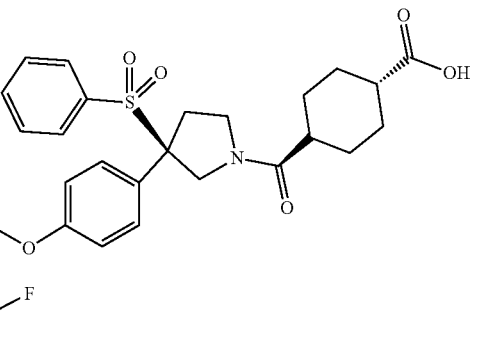<br>(1r,4r)-4-[(3R)-3-benzenesulfonyl)-3-(4-{[2-fluoro-6-(trifluoromethyl)phenyl]methoxy}phenyl)pyrrolidine-1-carbonyl]-cyclohexane-1-carboxylic acid | Method B: rt = 2.01 min; Obs. Adduct: [M + H]; Obs. Mass: 634.34; Method A: rt = 1.7 min; Obs. Adduct: [M + H]; Obs. Mass: 634.05 | 3 |
| 42 | 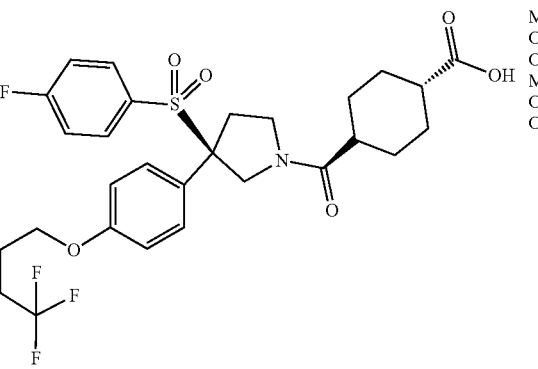<br>(1r,4r)-4-[(3R)-3-(4-{[2-fluoro-6-(trifluoromethyl)phenyl]methoxy}phenyl)-3-(4-fluorobenzenesulfonyl)pyrrolidine-1-carbonyl]-cyclohexane-1-carboxylic acid | Method A: rt = 1.74 min; Obs. Adduct: [M + H]; Obs. Mass: 652.29; Method B: rt = 2.06 min; Obs. Adduct: [M + H]; Obs. Mass: 652.3 | 3 |

| Example | Structure & Name | Analytical Data | Procedure Analogous to Example No. |
|---|---|---|---|
| 43 | 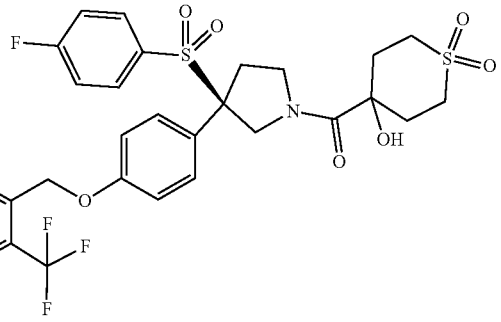<br>4-[(3R)-3-(4-{[2-(fluoro-6-(trifluoromethyl)phenyl]methoxy}phenyl)-3-(4-fluorobenzenesulfonyl)pyrrolidine-1-carbonyl]-4-hydroxy-1λ$^6$-thiane-1,1-dione | Method A: rt = 1.98 min;<br>Obs. Adduct: [M + H];<br>Obs. Mass: 674.16;<br>Method B: rt = 1.93 min;<br>Obs. Adduct: [M + H];<br>Obs. Mass: 674.32 | 3 |
| 44 | 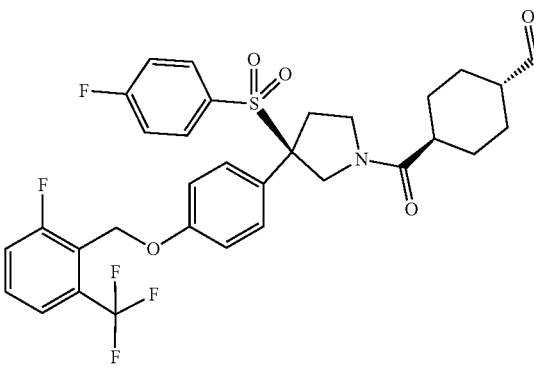<br>(1r,4r)-4-[(3R)-3-(4-{[2-fluoro-6-(trifluoromethyl)phenyl]methoxy}phenyl)-3-(4-fluorobenzenesulfonyl)pyrrolidine-1-carbonyl]-cyclohexane-1-carboxamide | Method A: rt = 1.9 min;<br>Obs. Adduct: [M + H];<br>Obs. Mass: 651.13;<br>Method B: rt = 1.94 min;<br>Obs. Adduct: [M + H];<br>Obs. Mass: 651 | 3 |
| 45 | 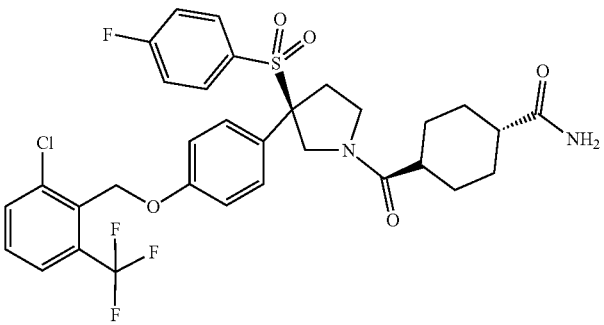<br>(1r,4r)-4-[(3R)-3-(4-{[2-chloro-6-(trifluoromethyl)phenyl]methoxy}phenyl)-3-(4-fluorobenzenesulfonyl)pyrrolidine-1-carbonyl]-cyclohexane-1-carboxamide | Method A: rt = 1.93 min;<br>Obs. Adduct: [M + H];<br>Obs. Mass: 667.29;<br>Method B: rt = 1.92 min;<br>Obs. Adduct: [M + H];<br>Obs. Mass: 667.28 | 3 |

-continued

| Example | Structure & Name | Analytical Data | Procedure Analogous to Example No. |
|---|---|---|---|
| 46 | 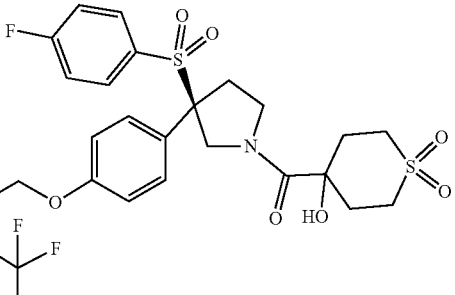<br>(4-[(3R)-3-(4-{[2-chloro-6-(trifluoromethyl)phenyl]methoxy}phenyl)-3-(4-fluorobenzenesulfonyl)pyrrolidine-1-carbonyl]-4-hydroxy-1$\lambda^6$-thiane-1,1-dione | Method B: rt = 2.05 min;<br>Obs. Adduct: [M + H];<br>Obs. Mass: 690.19;<br>Method A: rt = 1.99 min;<br>Obs. Adduct: [M + H];<br>Obs. Mass: 690.3 | 3 |
| 47 | 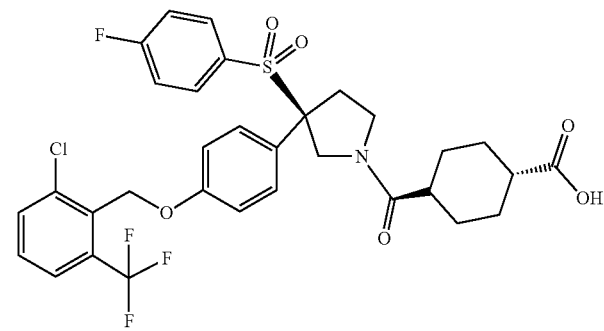<br>(1r,4r)-4-[(3R)-3-(4-{[2-chloro-6-(trifluoromethyl)phenyl]methoxy}phenyl)-3-(4-fluorobenzenesulfonyl)pyrrolidine-1-carbonyl]-cyclohexane-1-carboxylic acid | Method A: rt = 1.75 min;<br>Obs. Adduct: [M + H];<br>Obs. Mass: 668.32;<br>Method B: rt = 2.04 min;<br>Obs. Adduct: [M + H];<br>Obs. Mass: 668.12 | 3 |

Biological Assay

RORgT Gal4 Luciferase Reporter Gene Assay

The inhibition potency of each final compound was determined using engineered Jurkat cells overexpressing constitutively active RORgT proteins fused with Gal4 Luc reporter (Jurkat pEx/Gal/hRORγ CLBD/HYG pG5luc/blast). 25 μL of cryopreserved Jurkat cells over expressing ligand binding domain (LBD) of RORgT (aa267-516, NM_005060) and Gal4 Luc, or full length of human RORgT and Gal4 Luc, were plated in 384-well solid white cell culture plates (PerkinElmer 6007899), with a density of 10,000 cells/well in RPMI 1640 cell culture media (Gibco 11875-085). The media contained 0.1% BSA, 10 mM HEPES (Gibco 15360-080), 100 mM Sodium Pyruvate (Gibco 11360-040), 50 mg/mL Hygromycin B (Invitrogen 10687-010), and 10 mg/mL Blasticidin (Invitrogen R210-01).

100 nL of compound at varying concentrations in 3-fold serial dilution, with final concentrations ranging from 40 μM to 0.67 nM, were added to the cells using Labcyte Echo 550.

The compound and the cells were incubated for 18 hours at 37° C. in a cell culture incubator. Cells were then lysed with 15 uL of Steady-Glo Luciferase Assay reagent (Promega EZ550), followed by centrifuging the assay plates at 1500 RPM for 1 minute. Subsequently, the plates were read on the Envision (PerkinElmer). The inhibition of constitutive activity of RORgT achieved by graded concentrations of compound was calculated as a percentage of the luminescence signal window reduction over a control compound.

| Example No. | RORgT-GAL4 Agonist EC$_{50}$ (nM) |
|---|---|
| 1 | 214 |
| 2 | 123 |
| 3 | 27 |
| 4 | 139 |
| 5 | 240 |
| 6 | 130 |
| 7 | 723 |

| Example No. | RORgT-GAL4 Agonist EC$_{50}$ (nM) |
|---|---|
| 8 | 382 |
| 9 | 212 |
| 10 | 328 |
| 11 | 397 |
| 12 | 87 |
| 13 | 203 |
| 14 | 423 |
| 15 | 623 |
| 16 | 474 |
| 17 | 526 |
| 18 | 532 |
| 19 | 672 |
| 20 | 810 |
| 21 | 462 |
| 22 | 514 |
| 23 | 46 |
| 24 | 552 |
| 25 | 267 |
| 26 | 77 |
| 27 | 109 |
| 28 | 187 |
| 29 | 39 |
| 30 | 28 |
| 31 | 343 |
| 32 | 84 |
| 33 | 32 |
| 34 | 275 |
| 35 | 58 |
| 36 | 17 |
| 37 | 77 |
| 38 | 68 |
| 39 | 31 |
| 40 | 18 |
| 41 | 88 |
| 42 | 47 |
| 43 | 14 |
| 44 | 195 |
| 45 | 351 |
| 46 | 42 |
| 47 | 293 |

We claim:

1. A compound of the formula

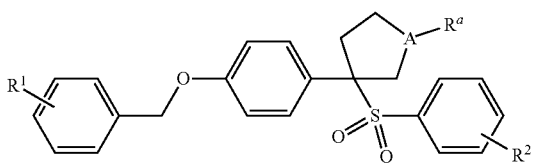

wherein

A is —CH— or —N—;

$R^a$ is H or CO—$R^b$, $R^b$ is a $C_{3-8}$ cycloalkyl or a —(CH$_2$)$_r$-3-7 membered heterocycle either of which is substituted with 0-3 $R^c$;

$R^c$ is halogen, $C_{1-6}$ alkyl, COOH or CONH$_2$, $R^1$ and $R^2$ are independently 0-4 hydrogen, halogen, $C_{1-6}$ alkyl or CF$_3$;

r is 0, 1 or 2;

or a pharmaceutically acceptable salt thereof.

2. The compound according to claim 1 of the formula

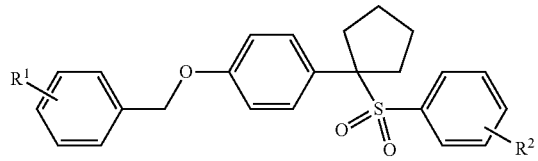

wherein $R^1$ and $R^2$ are independently 0-4 hydrogen, halogen, $C_{1-6}$ alkyl or CF$_3$;

or a pharmaceutically acceptable salt thereof.

3. The compound according to claim 1 of the formula

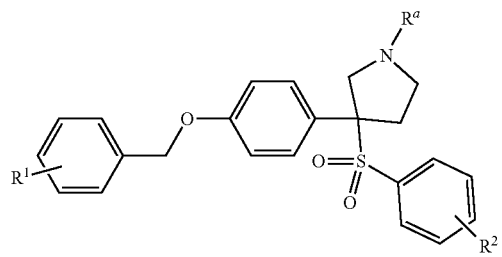

wherein $R^a$ is CO—$R^b$, $R^b$ is a $C_{3-8}$ cycloalkyl or a —(CH$_2$)$_r$-3-7 membered heterocycle either of which is substituted with 0-3 $R^c$;

$R^c$ is hydrogen, halogen, $C_{1-6}$ alkyl, COOH or CONH$_2$, $R^1$ and $R^2$ are independently 0-4 hydrogen, halogen, $C_{1-6}$ alkyl or CF$_3$;

r is 0, 1 or 2;

or a pharmaceutically acceptable salt thereof.

4. The compound according to claim 3 wherein $R^a$ is CO—$R^b$, $R^b$ is a $C_{3-8}$ cycloalkyl substituted with 0-3 $R^c$;

$R^c$ is hydrogen, halogen, $C_{1-6}$ alkyl, COOH or CONH$_2$, $R^1$ and $R^2$ are independently 0-4 hydrogen, halogen, $C_{1-6}$ alkyl or CF$_3$;

or a pharmaceutically acceptable salt thereof.

5. The compound according to claim 3 wherein $R^a$ is CO—$R^b$, $R^b$ is a —(CH$_2$)$_r$-3-7 membered heterocycle substituted with 0-3 $R^c$;

$R^c$ is hydrogen, halogen, $C_{1-6}$ alkyl, COOH or CONH$_2$, $R^1$ and $R^2$ are independently 0-4 hydrogen, halogen, $C_{1-6}$ alkyl or CF$_3$;

r is 0, 1 or 2;

or a pharmaceutically acceptable salt thereof.

6. The compound according to claim 5 wherein $R^a$ is CO—$R^b$, $R^b$ is a —(CH$_2$)$_r$-3-7 membered heterocycle substituted with 0-3 $R^c$;

$R^c$ is hydrogen, halogen, $C_{1-6}$ alkyl, COOH or CONH$_2$, $R^1$ and $R^2$ are independently 0-4 hydrogen, halogen, $C_{1-6}$ alkyl or CF$_3$;

r is 1;

or a pharmaceutically acceptable salt thereof.

7. The compound according to claim 5 wherein $R^a$ is CO—$R^b$, $R^b$ is a —(CH$_2$)$_r$-3-7 membered heterocycle substituted with 0-3 $R^c$, wherein the heterocycle is selected from the group consisting of oxanyl, pyridinyl, triazolyl, thiolane-1,1-dione, thiazolidine-2,4-dione or thiane-1,1-dione;
$R^c$ is hydrogen, halogen, $C_{1-6}$ alkyl, COOH or $CONH_2$,
$R^1$ and $R^2$ are independently 0-4 hydrogen, halogen, $C_{1-6}$ alkyl or $CF_3$;
r is 1;
or a pharmaceutically acceptable salt thereof.

8. A compound according to claim 1 which is
1-(benzyloxy)-4-(1-((4-fluorophenyl)sulfonyl)cyclopentyl)benzene,
4-{3-[4-(benzyloxy)phenyl]-3-(4-fluorobenzenesulfonyl)pyrrolidine-1-carbonyl}-1lambda6-thiane-1,1-dione, (2)
4-[(3R)-3-(4-{[2-fluoro-6-(trifluoromethyl)phenyl]methoxy}phenyl)-3-(4-fluorobenzenesulfonyl)pyrrolidine-1-carbonyl]-1lambda6-thiane-1,1-dione, (3)
1-[1-(4-fluorobenzenesulfonyl)cyclopentyl]-4-(2-phenylethoxy)benzene, (4)
1-(benzyloxy)-4-[1-(3-chlorobenzenesulfonyl)cyclopentyl]benzene,
1-[1-(benzenesulfonyl)cyclopentyl]-4-(benzyloxy)benzene,
1-[1-(4-fluorobenzenesulfonyl)cyclopentyl]-4-[(2-fluorophenyl)methoxy]benzene,
1-(benzyloxy)-4-{1-[3-(trifluoromethyl)benzenesulfonyl]cyclopentyl}benzene,
1-(benzyloxy)-4-[1-(4-chlorobenzenesulfonyl)cyclopentyl]benzene,
1-[1-(benzenesulfonyl)cyclopentyl]-4-(cyclohexylmethoxy)benzene, (10)
1-[1-(benzenesulfonyl)cyclopentyl]-4-[(3-fluorophenyl)methoxy]benzene,
1-[1-(benzenesulfonyl)cyclopentyl]-4-[(4-fluorophenyl)methoxy]benzene,
1-[1-(benzenesulfonyl)cyclopentyl]-4-[(2-fluorophenyl)methoxy]benzene,
1-[1-(benzenesulfonyl)cyclopentyl]-4-(2-cyclopropylethoxy)benzene, (14)
1-{3-[4-(benzyloxy)phenyl]-3-(4-fluorobenzenesulfonyl)pyrrolidin-1-yl}-2-(oxan-4-yl)ethan-1-one,
1-{3-[4-(benzyloxy)phenyl]-3-(4-fluorobenzenesulfonyl)pyrrolidin-1-yl}-2-(pyridin-4-yl)ethan-1-one,
1-{3-[4-(benzyloxy)phenyl]-3-(4-fluorobenzenesulfonyl)pyrrolidin-1-yl}-2-(1H-1,2,3-triazol-1-yl)ethan-1-one,
3-[4-(benzyloxy)phenyl]-3-(4-fluorobenzenesulfonyl)-1-(oxane-4-carbonyl)pyrrolidine,
3-{3-[4-(benzyloxy)phenyl]-3-(4-fluorobenzenesulfonyl)pyrrolidine-1-carbonyl}-1$\lambda^6$-thiolane-1,1-dione,
5-(2-{3-[4-(benzyloxy)phenyl]-3-(4-fluorobenzenesulfonyl)pyrrolidin-1-yl}-2-oxoethyl)-1,3-thiazolidine-2,4-dione,
4-{3-[4-(benzyloxy)phenyl]-3-[3-(trifluoromethyl)benzenesulfonyl]pyrrolidine-1-carbonyl}-1$\lambda^6$-thiane-1,1-dione,
1-{3-[4-(benzyloxy)phenyl]-3-[3-(trifluoromethyl)benzenesulfonyl]pyrrolidin-1-yl}-2-(pyridin-4-yl)ethan-1-one,
4-[3-(benzenesulfonyl)-3-{4-[(2,6-dichlorophenyl)methoxy]phenyl}pyrrolidine-1-carbonyl]-1$\lambda^6$-thiane-1,1-dione,
(1r,4r)-4-[3-(benzenesulfonyl)-3-{4-[(2,6-dichlorophenyl)methoxy]phenyl}pyrrolidine-1-carbonyl]cyclohexane-1-carboxylic acid,
4-[3-(benzenesulfonyl)-3-{4-[(2,6-dichlorophenyl)methoxy]phenyl}pyrrolidine-1-carbonyl]piperidine-1-carboxamide,
1-[3-(benzenesulfonyl)-3-{4-[(2,6-dichlorophenyl)methoxy]phenyl}pyrrolidin-1-yl]-2-(pyridin-4-yl)ethan-1-one,
4-[3-(benzenesulfonyl)-3-{4-[(2-chloro-3,6-difluorophenyl)methoxy]phenyl}pyrrolidine-1-carbonyl]-1$\lambda^6$-thiane-1,1-dione,
4-[3-(benzenesulfonyl)-3-{4-[(2-chlorophenyl)methoxy]phenyl}pyrrolidine-1-carbonyl]-1$\lambda^6$-thiane-1,1-dione,
4-[3-(benzenesulfonyl)-3-{4-[(2-chloro-6-fluorophenyl)methoxy]phenyl}pyrrolidine-1-carbonyl]-1$\lambda^6$-thiane-1,1-dione,
4-[3-(benzenesulfonyl)-3-(4-{[2-fluoro-6-(trifluoromethyl)phenyl]methoxy}phenyl)pyrrolidine-1-carbonyl]-1$\lambda^6$-thiane-1,1-dione,
4-[3-(benzenesulfonyl)-3-{4-[(2-chloro-4-fluorophenyl)methoxy]phenyl}pyrrolidine-1-carbonyl]-1$\lambda^6$-thiane-1,1-dione,
4-[3-(benzenesulfonyl)-3-(4-{[2-(trifluoromethyl)phenyl]methoxy}phenyl)pyrrolidine-1-carbonyl]-1$\lambda^6$-thiane-1,1-dione,
4-[(3R)-3-(benzenesulfonyl)-3-{4-[(2,6-dichlorophenyl)methoxy]phenyl}pyrrolidine-1-carbonyl]-1$\lambda^6$-thiane-1,1-dione,
(1r,4r)-4-[(3R)-3-(benzenesulfonyl)-3-{4-[(2,6-dichlorophenyl)methoxy]phenyl}pyrrolidine-1-carbonyl]cyclohexane-1-carboxylic acid,
(1r,4r)-4-[(3R)-3-{4-[(2,6-dichlorophenyl)methoxy]phenyl}-3-(4-fluorobenzenesulfonyl)pyrrolidine-1-carbonyl]cyclohexane-1-carboxylic acid,
4-[(3R)-3-{4-[(2,6-dichlorophenyl)methoxy]phenyl}-3-(4-fluorobenzenesulfonyl)pyrrolidine-1-carbonyl]-1$\lambda^6$-thiane-1,1-dione,
4-[(3R)-3-(4-fluorobenzenesulfonyl)-3-{4-[(1S)-1-phenylethoxy]phenyl}pyrrolidine-1-carbonyl]-1$\lambda^6$-thiane-1,1-dione, (37)
4-[(3R)-3-(4-fluorobenzenesulfonyl)-3-(4-{[2-(trifluoromethyl)phenyl]methoxy}phenyl)pyrrolidine-1-carbonyl]-1$\lambda^6$-thiane-1,1-dione,
4-[(3R)-3-(4-{[2-chloro-6-(trifluoromethyl)phenyl]methoxy}phenyl)-3-(4-fluorobenzenesulfonyl)pyrrolidine-1-carbonyl]-1$\lambda^6$-thiane-1,1-dione,
4-[(3R)-3-(benzenesulfonyl)-3-(4-{[2-fluoro-6-(trifluoromethyl)phenyl]methoxy}phenyl)pyrrolidine-1-carbonyl]-4-hydroxy-1$\lambda^6$-thiane-1,1-dione,
(1r,4r)-4-[(3R)-3-(benzenesulfonyl)-3-(4-{[2-fluoro-6-(trifluoromethyl)phenyl]methoxy}phenyl)pyrrolidine-1-carbonyl]cyclohexane-1-carboxylic acid,
(1r,4r)-4-[(3R)-3-(4-{[2-fluoro-6-(trifluoromethyl)phenyl]methoxy}phenyl)-3-(4-fluorobenzenesulfonyl)pyrrolidine-1-carbonyl]cyclohexane-1-carboxylic acid,
4-[(3R)-3-(4-{[2-fluoro-6-(trifluoromethyl)phenyl]methoxy}phenyl)-3-(4-fluorobenzenesulfonyl)pyrrolidine-1-carbonyl]-4-hydroxy-1$\lambda^6$-thiane-1,1-dione,
(1r,4r)-4-[(3R)-3-(4-{[2-fluoro-6-(trifluoromethyl)phenyl]methoxy}phenyl)-3-(4-fluorobenzenesulfonyl)pyrrolidine-1-carbonyl]cyclohexane-1-carboxamide,
(1r,4r)-4-[(3R)-3-(4-{[2-chloro-6-(trifluoromethyl)phenyl]methoxy}phenyl)-3-(4-fluorobenzenesulfonyl)pyrrolidine-1-carbonyl]cyclohexane-1-carboxamide,
4-[(3R)-3-(4-{[2-chloro-6-(trifluoromethyl)phenyl]methoxy}phenyl)-3-(4-fluorobenzenesulfonyl)pyrrolidine-1-carbonyl]-4-hydroxy-1$\lambda^6$-thiane-1,1-dione,
(1r,4r)-4-[(3R)-3-(4-{[2-chloro-6-(trifluoromethyl)phenyl]methoxy}phenyl)-3-(4-fluorobenzenesulfonyl)pyrrolidine-1-carbonyl]cyclohexane-1-carboxylic acid
or a pharmaceutically acceptable salt thereof.

9. A compound which is
1-[1-(4-fluorobenzenesulfonyl)cyclopentyl]-4-(2-phenylethoxy)benzene, (4)
1-[1-(benzenesulfonyl)cyclopentyl]-4-(cyclohexylmethoxy)benzene, (10)
1-[1-(benzenesulfonyl)cyclopentyl]-4-(2-cyclopropylethoxy)benzene, (14)
4-[(3R)-3-(4-fluorobenzenesulfonyl)-3-{4-[(1S)-1-phenylethoxy]phenyl}pyrrolidine-1-carbonyl]-1$\lambda^6$-thiane-1,1-dione, (37)
or a pharmaceutically acceptable salt thereof.

10. A pharmaceutical composition comprising one or more compounds according to claim 1 or a pharmaceutically acceptable salt thereof and one or more pharmaceutically acceptable carriers, diluents or excipients.

\* \* \* \* \*